(12) United States Patent
Lin et al.

(10) Patent No.: US 11,389,655 B2
(45) Date of Patent: Jul. 19, 2022

(54) ADAPTIVE CHRONIC PAIN RELIEF VIA IMPLANTED ELECTRICAL NEUROSTIMULATION

(71) Applicant: Boston Scientific Neuromodulation Corporation, Valencia, CA (US)

(72) Inventors: Qinghuang Lin, Yorktown Heights, NY (US); Jeffrey Rogers, Briarcliff Manor, NY (US); Giovanni Russo, Smithfield Market (IE); Andrea Simonetto, Leixlip (IE); Tigran Tchrakian, Castleknock (IE)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 40 days.

(21) Appl. No.: 16/417,516

(22) Filed: May 20, 2019

(65) Prior Publication Data
US 2019/0358455 A1    Nov. 28, 2019

Related U.S. Application Data

(60) Provisional application No. 62/674,991, filed on May 22, 2018.

(51) Int. Cl.
*A61N 1/00*    (2006.01)
*A61N 1/36*    (2006.01)
(Continued)

(52) U.S. Cl.
CPC ........ *A61N 1/36071* (2013.01); *A61B 5/0205* (2013.01); *A61B 5/112* (2013.01);
(Continued)

(58) Field of Classification Search
None
See application file for complete search history.

(56) References Cited

U.S. PATENT DOCUMENTS 5,908,383 A    6/1999  Brynjestad
7,229,430 B2   6/2007  Hickle et al.
(Continued)

FOREIGN PATENT DOCUMENTS

WO   WO-2016113661 A1   7/2016
WO   WO-2017117421 A1   7/2017
(Continued)

OTHER PUBLICATIONS

Wang, Y., & Winters, J. (Jun. 28, 2005). A dynamic neuro-fuzzy model providing bio-state estimation and prognosis prediction for wearable intelligent assistants. Retrieved Mar. 18, 2021, from https://www.ncbi.nlm.nih.gov/pmc/articles/PMC1182386/ (Year: 2005).*
(Continued)

*Primary Examiner* — Gary Jackson
*Assistant Examiner* — Anant A Gupta
(74) *Attorney, Agent, or Firm* — Schwegman Lundberg & Woessner, P.A.

(57) ABSTRACT

Systems and techniques are disclosed to adjust programming of an implantable electrical neurostimulation device for treating chronic pain of a human subject, through the use of a dynamic model adapted to identify pain treatment parameters for a human patient and determine a best device operational program to implement the pain treatment parameters to address the chronic pain condition. In an example, the system to adjust programming of the neurostimulation device performs operations that: obtain data related to a state of pain of the human subject; identify pain treatment parameters using a dynamic model adapted to evaluate the pain treatment parameters in the human subject over a time period, based on the data related to the state of pain; and select a neurostimulation program for the neurostimulation device, corresponding to at least a portion of the identified pain treatment parameters.

20 Claims, 8 Drawing Sheets

(51) Int. Cl.

| | |
|---|---|
| *A61B 5/0205* | (2006.01) |
| *A61B 5/11* | (2006.01) |
| *A61B 5/16* | (2006.01) |
| *A61B 5/00* | (2006.01) |
| *A61N 1/05* | (2006.01) |
| *A61N 1/372* | (2006.01) |
| *A61B 5/021* | (2006.01) |
| *A61B 5/08* | (2006.01) |

(52) U.S. Cl.
CPC ............ *A61B 5/165* (2013.01); *A61B 5/4824* (2013.01); *A61N 1/0551* (2013.01); *A61N 1/36132* (2013.01); *A61N 1/36139* (2013.01); *A61N 1/37217* (2013.01); *A61N 1/37247* (2013.01); *A61N 1/37264* (2013.01); *A61B 5/021* (2013.01); *A61B 5/0816* (2013.01); *A61N 1/0534* (2013.01)

(56) References Cited

U.S. PATENT DOCUMENTS

| | | | |
|---|---|---|---|
| 7,463,927 | B1 | 12/2008 | Chaouat |
| 7,957,809 | B2 | 6/2011 | Bourget et al. |
| 8,046,241 | B1 | 10/2011 | Dodson |
| 8,086,563 | B2 | 12/2011 | Jung et al. |
| 8,380,314 | B2 | 2/2013 | Panken et al. |
| 8,380,531 | B2 | 2/2013 | Paty et al. |
| 8,469,713 | B2 | 6/2013 | Kron et al. |
| 9,147,041 | B2 | 9/2015 | Amarasingham et al. |
| 9,262,688 | B1 | 2/2016 | Zadeh |
| 9,452,294 | B2 | 9/2016 | Kaula et al. |
| 9,536,049 | B2 | 1/2017 | Brown et al. |
| 9,636,273 | B1 | 5/2017 | Harris |
| 9,782,122 | B1 | 10/2017 | Pulliam et al. |
| 10,449,371 | B2 * | 10/2019 | Serrano Carmona ........................ A61N 1/36071 |
| 11,033,740 | B2 * | 6/2021 | Lin .................... A61N 1/37247 |
| 2001/0012913 | A1 | 8/2001 | Iliff |
| 2002/0128866 | A1 | 9/2002 | Goetzke et al. |
| 2003/0178031 | A1 | 9/2003 | Du Pen et al. |
| 2004/0064709 | A1 | 4/2004 | Heath |
| 2006/0293572 | A1 | 12/2006 | Bulat |
| 2007/0271272 | A1 | 11/2007 | Mcguire et al. |
| 2008/0059241 | A1 | 3/2008 | Zahlmann et al. |
| 2009/0157141 | A1 | 6/2009 | Chiao et al. |
| 2010/0087795 | A1 | 4/2010 | Krijnsen et al. |
| 2010/0153832 | A1 | 6/2010 | Markus et al. |
| 2011/0035158 | A1 | 2/2011 | Banos et al. |
| 2011/0054564 | A1 | 3/2011 | Valencia |
| 2012/0078837 | A1 | 3/2012 | Bagchi et al. |
| 2013/0066394 | A1 | 3/2013 | Saab |
| 2013/0173277 | A1 | 7/2013 | Eller et al. |
| 2013/0244336 | A1 | 9/2013 | Mayer et al. |
| 2014/0074454 | A1 | 3/2014 | Brown et al. |
| 2014/0074509 | A1 | 3/2014 | Amarasingham et al. |
| 2014/0275827 | A1 | 9/2014 | Gill et al. |
| 2014/0276188 | A1 | 9/2014 | Jardin |
| 2014/0316793 | A1 | 10/2014 | Pruit |
| 2015/0012057 | A1 * | 1/2015 | Carlson .............. A61N 1/37264 607/45 |
| 2015/0066111 | A1 | 3/2015 | Blum et al. |
| 2015/0199484 | A1 | 7/2015 | Morris et al. |
| 2015/0254408 | A1 | 9/2015 | Dadlani Mahtani et al. |
| 2015/0287330 | A1 | 10/2015 | Kron et al. |
| 2016/0100790 | A1 | 4/2016 | Cantu et al. |
| 2016/0198996 | A1 | 7/2016 | Dullen |
| 2016/0210424 | A1 | 7/2016 | Di Battista |
| 2016/0213314 | A1 | 7/2016 | Zuckerman-stark et al. |
| 2016/0335412 | A1 | 11/2016 | Tucker et al. |
| 2016/0339241 | A1 | 11/2016 | Hargrove et al. |
| 2017/0004260 | A1 | 1/2017 | Moturu et al. |
| 2017/0056642 | A1 | 3/2017 | Moffitt et al. |
| 2017/0080234 | A1 * | 3/2017 | Gillespie ............ A61N 1/37247 |
| 2017/0189686 | A1 | 7/2017 | Steinke et al. |
| 2017/0189689 | A1 | 7/2017 | Steinke et al. |
| 2018/0039763 | A1 | 2/2018 | Tidor |
| 2018/0043172 | A1 | 2/2018 | Serrano Carmona |
| 2019/0140986 | A1 | 5/2019 | Anderson et al. |
| 2019/0358454 | A1 | 11/2019 | Lin et al. |
| 2021/0252288 | A1 | 8/2021 | Lin et al. |

FOREIGN PATENT DOCUMENTS

| | | |
|---|---|---|
| WO | WO-2019226564 A1 | 11/2019 |
| WO | WO-2019226568 A1 | 11/2019 |

OTHER PUBLICATIONS

Wang, Y., & Winters, J. (Jun. 28, 2005). A dynamic neuro-fuzzy model providing bio-state estimation and prognosis prediction for wearable intelligent assistants. https://www.ncbi.nlm.nih.gov/pmc/articles/PMC1182386/ (Year: 2005).*

"U.S. Appl. No. 16/417,476, Non Final Office Action dated Oct. 13, 2020", 16 pgs.

"U.S. Appl. No. 16/417,476, Response filed Jan. 13, 2021 to Non Final Office Action dated Oct. 13, 2020", 14 pgs.

"International Application Serial No. PCT/US2019/033154, International Preliminary Report on Patentability dated Dec. 3, 2020", 10 pgs.

"International Application Serial No. PCT/US2019/033154, International Search Report dated Jul. 23, 2019", 5 pgs.

"International Application Serial No. PCT/US2019/033154, Written Opinion dated Jul. 23, 2019", 8 pgs.

"International Application Serial No. PCT/US2019/033164, International Preliminary Report on Patentability dated Dec. 3, 2020", 9 pgs.

"International Application Serial No. PCT/US2019/033164, International Search Report dated Aug. 16, 2019", 5 pgs.

"International Application Serial No. PCT/US2019/033164, Written Opinion dated Aug. 16, 2019", 7 pgs.

"U.S. Appl. No. 16/417,476, Examiner Interview Summary dated Jan. 19, 2021", 2 pgs.

"U.S. Appl. No. 16/417,476, Notice of Allowance dated Feb. 10, 2021", 9 pgs.

"Australian Application Serial No. 2019274427, First Examination Report dated Jun. 11, 2021", 3 pgs.

"Australian Application Serial No. 2019275411, First Examination Report dated Jun. 15, 2021", 4 pgs.

"Dynamics (mechanics)", Wikipedia, <https://en.wikipedia.org/wiki/Dynamics (mechanics)>, (2021).

"Australian Application Serial No. 2019275411, Response filed Dec. 3, 2021 to First Examination Report dated Jun. 15, 2021", 15 pgs.

"Canadian Application Serial No. 3,099,523, Office Action dated Nov. 5, 2021", 5 pgs.

"Canadian Application Serial No. 3,100,748 , Office Action dated Nov. 12, 2021", 6 pgs.

"European Application Serial No. 19728837.6, Response filed Jul. 21, 2021 to Communication pursuant to Rules 161(1) and 162 EPC dated Jan. 19, 2021", 16 pgs.

"European Application Serial No. 19729134.7, Response filed Jul. 15, 2021 Communication pursuant to Rules 161(1) and 162 EPC dated Jul. 15, 2021", 15 pgs.

"Canadian Application Serial No. 3,100,748, Office Action dated May 24, 2022", 4 pgs.

* cited by examiner

ADAPTIVE CHRONIC PAIN RELIEF VIA IMPLANTED ELECTRICAL NEUROSTIMULATION

CLAIM OF PRIORITY

This application claims the benefit of priority under 35 U.S.C. § 119(e) of U.S. Provisional Patent Application Ser. No. 62/674,991, filed on May 22, 2018, and titled "ADAPTIVE CHRONIC PAIN RELIEF VIA IMPLANTED ELECTRICAL NEUROSTIMULATION", which is incorporated by reference herein in its entirety.

DISCLAIMER

The claims and scope of the subject application, and any continuation, divisional or continuation-in-part applications claiming priority to the subject application, are solely limited to embodiments (e.g., systems, apparatus, methodologies, computer program products and computer readable storage media) directed to implanted electrical stimulation for pain treatment and/or management.

STATEMENT REGARDING JOINT RESEARCH AND DEVELOPMENT

The present subject matter was developed and the claimed invention was made by or on behalf of Boston Scientific Neuromodulation Corporation and International Business Machines Corporation, parties to a joint research agreement that was in effect on or before the effective filing date of the claimed invention, and the claimed invention was made as a result of activities undertaken within the scope of the joint research agreement.

TECHNICAL FIELD

The present disclosure relates generally to medical devices, and more particularly, to systems, devices, and methods for electrical stimulation programming techniques, to perform implanted electrical stimulation for pain treatment and/or management.

BACKGROUND

Neurostimulation, also referred to as neuromodulation, has been proposed as a therapy for a number of conditions. Examples of neurostimulation include Spinal Cord Stimulation (SCS), Deep Brain Stimulation (DBS), Peripheral Nerve Stimulation (PNS), and Functional Electrical Stimulation (FES). Implantable neurostimulation systems have been applied to deliver such a therapy. An implantable electrical neurostimulation system may include an implantable neurostimulator, also referred to as an implantable pulse generator (IPG), and one or more implantable leads each including one or more electrodes. The implantable neurostimulator delivers neurostimulation energy through one or more electrodes placed on or near a target site in the nervous system.

A neuromodulation system can be used to electrically stimulate tissue or nerve centers to treat nervous or muscular disorders. For example, an SCS system may be configured to deliver electrical pulses to a specified region of a patient's spinal cord, such as particular spinal nerve roots or nerve bundles, to create an analgesic effect that masks pain sensation. While modern electronics can accommodate the need for generating and delivering stimulation energy in a variety of forms, the capability of a neurostimulation system depends on its post-manufacturing programmability to a great extent. For example, a sophisticated neurostimulation program may only benefit a patient when it is customized for that patient, and stimulation patterns or programs of patterns that are predetermined at the time of manufacturing may substantially limit the potential for the customization.

SUMMARY

This Summary includes examples that provide an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

Example 1 is a system for use to adjust programming of an implantable electrical neurostimulation device for treating chronic pain of a human subject, the system comprising: at least one processor; and at least one memory device storing instructions, which when executed by the processor, cause the at least one processor to perform operations that: obtain data related to a state of pain of the human subject; identify pain treatment parameters using a dynamic model, the dynamic model adapted to evaluate the pain treatment parameters in the human subject over a time period, based on the data related to the state of pain; and select a neurostimulation program for the implantable electrical neurostimulation device, the neurostimulation program corresponding to at least a portion of the identified pain treatment parameters.

In Example 2, the subject matter of Example 1 includes, instructions further to cause operations that: identify a measured pain level and a predicted pain level of the human subject using the data related to the state of pain; wherein the operations that identify the pain treatment parameters using the dynamic model evaluate at least the measured pain level and the predicted pain level; and wherein the data related to the state of pain of the human subject comprises data obtained from the human subject that includes at least one of: physiological data, activity data, or behavior data.

In Example 3, the subject matter of Example 2 includes, the state of pain of the human subject being determined from physiological data, which includes values that indicate of one or more of: autonomic tone, heart rate, respiratory rate, or blood pressure, for the human subject.

In Example 4, the subject matter of Examples 2-3 includes, the state of pain of the human subject being determined from activity data, wherein the activity data includes values that indicate of at least one of: movement or gait for the human subject.

In Example 5, the subject matter of Examples 2-4 includes, the state of pain of the human subject being determined from behavior data, and wherein the behavior data includes values that indicate of one or more of: a psychological state of the human subject or social activities performed by the human subject.

In Example 6, the subject matter of Examples 1-5 includes, the dynamic model being further adapted to evaluate the pain treatment parameters in the human subject based on operational data obtained from use or programming of the implantable electrical neurostimulation device.

In Example 7, the subject matter of Examples 1-6 includes, the dynamic model is a continuous time model or a discrete time model, wherein the dynamic model evaluates the pain treatment parameters in the human subject over the time period based on: predicted pain of the human subject, observed pain of the human subject, dynamic model parameters, and operational data of the implantable electrical neurostimulation device.

In Example 8, the subject matter of Examples 1-7 includes, instructions further to cause operations that: receive, from the human subject, feedback data on the selected neurostimulation program, the feedback data received in response to deployment of the selected neurostimulation program to the human subject using the implantable electrical neurostimulation device; wherein subsequent operations using the dynamic model evaluate the feedback data as dynamic model parameters.

In Example 9, the subject matter of Examples 1-8 includes, the pain treatment parameters being stored by a data service, and wherein subsequent operations using the dynamic model obtain the pain treatment parameters from the data service and evaluate the pain treatment parameters obtained from the data service.

In Example 10, the subject matter of Examples 1-9 includes, a user interface that is used to receive at least one of: at least a portion of the data related to a state of pain of the human subject, or a command to cause selection or deployment of the neurostimulation program.

In Example 11, the subject matter of Examples 1-10 includes, the selected neurostimulation program being one of a plurality of predefined neurostimulation programs available for use in the implantable electrical neurostimulation device; and wherein the dynamic model is one of a plurality of dynamic models available for identification of the pain treatment parameters, and wherein the dynamic model is selected from a dynamic model data source based on the data related to a state of pain of the human subject.

In Example 12, the subject matter of Examples 1-11 includes, the identified pain treatment parameters of the selected neurostimulation program causing a change in operation of the implantable electrical neurostimulation device, that corresponds to a change in the state of pain of the human subject.

In Example 13, the subject matter of Examples 1-12 includes, the identified pain treatment parameters of the selected neurostimulation program specifying a change in programming for the implantable electrical neurostimulation device for one or more of: pulse patterns, pulse shapes, a spatial location of pulses, waveform shapes, or a spatial location of waveform shapes, for modulated energy provided with a plurality of leads of the implantable electrical neurostimulation device.

In Example 14, the subject matter of Examples 1-13 includes, instructions further to cause the processor to: provide instructions to cause the implantable electrical neurostimulation device to implement the neurostimulation program.

In Example 15, the subject matter of Examples 1-14 includes, the implantable electrical neurostimulation device being further configured to treat pain by delivering at least one of: an electrical spinal cord stimulation, an electrical brain stimulation, or an electrical peripheral nerve stimulation, in the human subject.

Example 16 is a machine-readable medium including instructions, which when executed by a machine, cause the machine to perform the operations of the system of any of the Examples 1 to 15.

Example 17 is a method to perform the operations of the system of any of the Examples 1 to 15.

Example 18 is a device to adjust programming of an implantable electrical neurostimulation device for treating chronic pain of a human subject, the device comprising: at least one processor and at least one memory; pain determination circuitry, operable with the processor and the memory, configured to: obtain data related to a state of pain of the human subject; identify pain treatment parameters using a dynamic model, the dynamic model adapted to evaluate the pain treatment parameters in the human subject over a time period, based on the data related to the state of pain; and neurostimulation programming circuitry, in operation with the at least one processor and the at least one memory, configured to: select a neurostimulation program for the implantable electrical neurostimulation device, the neurostimulation program corresponding to at least a portion of the identified pain treatment parameters.

In Example 19, the subject matter of Example 18 includes, the pain determination circuitry further configured to: identify a measured pain level and a predicted pain level of the human subject using the data related to the state of pain; wherein operations that identify the pain treatment parameters using the dynamic model evaluate at least the measured pain level and the predicted pain level; and wherein the data related to the state of pain of the human subject comprises data obtained from the human subject that includes at least one of: physiological data, activity data, or behavior data.

In Example 20, the subject matter of Examples 18-19 includes, the pain determination circuitry further configured to: identify the state of pain of the human subject from evaluation of: physiological data that includes values to indicate at least one of: autonomic tone, heart rate, respiratory rate, or blood pressure, for the human subject; activity data that includes values to indicate of at least one of: movement or gait for the human subject; or behavior data that includes values to indicate at least one of: a psychological state of the human subject or social activities performed by the human subject.

In Example 21, the subject matter of Examples 18-20 includes, the pain determination circuitry further configured to: evaluate the pain treatment parameters in the human subject, with the dynamic model, based on operational data obtained from use or programming of the implantable electrical neurostimulation device.

In Example 22, the subject matter of Examples 18-21 includes, the dynamic model being a continuous time model or a discrete time model, wherein the dynamic model evaluates the pain treatment parameters in the human subject over the time period based on: predicted pain of the human subject, observed pain of the human subject, dynamic model parameters, and operational data of the implantable electrical neurostimulation device.

In Example 23, the subject matter of Examples 18-22 includes, user interface circuitry, in operation with the at least one processor and the at least one memory, configured to: receive, from the human subject, feedback data on the selected neurostimulation program, the feedback data received in response to deployment of the selected neurostimulation program to the human subject using the implantable electrical neurostimulation device; wherein subsequent operations using the dynamic model evaluate the feedback data as dynamic model parameters.

In Example 24, the subject matter of Example 23 includes, a user interface implemented with the user interface circuitry being used to receive at least one of: at least a portion of the data related to a state of pain of the human subject, or a command to cause selection or deployment of the neurostimulation program.

In Example 25, the subject matter of Examples 18-24 includes, communications circuitry, in operation with the at least one processor and the at least one memory; wherein the pain treatment parameters are stored by a data service, and wherein subsequent operations using the dynamic model obtain the pain treatment parameters from the data service and evaluate the pain treatment parameters received from the data service using the communications circuitry.

In Example 26, the subject matter of Examples 18-25 includes, the selected neurostimulation program being one of a plurality of predefined neurostimulation programs available for use in the implantable electrical neurostimulation device; and wherein the dynamic model is one of a plurality of dynamic models available for identification of the pain treatment parameters, and wherein the dynamic model is selected from a dynamic model data source based on the data related to a state of pain of the human subject.

In Example 27, the subject matter of Examples 18-26 includes, the implantable electrical neurostimulation device being further configured to treat pain by delivering at least one of: an electrical spinal cord stimulation, an electrical brain stimulation, or an electrical peripheral nerve stimulation, in the human subject; and wherein the identified pain treatment parameters of the selected neurostimulation program specifies a change in programming for the implantable electrical neurostimulation device for one or more of: pulse patterns, pulse shapes, a spatial location of pulses, waveform shapes, or a spatial location of waveform shapes, for modulated energy provided with a plurality of leads of the implantable electrical neurostimulation device.

Example 28 is a method, for adjusting programming of an implantable electrical neurostimulation device for treating chronic pain of a human subject, the method comprising a plurality of operations executed with at least one processor of an electronic device, the plurality of operations comprising: obtaining data related to a state of pain of the human subject; identifying pain treatment parameters using a dynamic model, the dynamic model adapted to evaluate the pain treatment parameters in the human subject over a time period, based on the data related to the state of pain; and selecting a neurostimulation program for the implantable electrical neurostimulation device, the neurostimulation program corresponding to at least a portion of the identified pain treatment parameters.

In Example 29, the subject matter of Example 28 includes, identifying a measured pain level and a predicted pain level of the human subject using the data related to the state of pain; wherein the operations that identify the pain treatment parameters using the dynamic model evaluate at least the measured pain level and the predicted pain level; and wherein the data related to the state of pain of the human subject comprises data obtained from the human subject that includes at least one of: physiological data, activity data, or behavior data.

In Example 30, the subject matter of Examples 28-29 includes, determining the state of pain of the human subject from: physiological data that includes values to indicate at least one of: autonomic tone, heart rate, respiratory rate, or blood pressure, for the human subject; activity data that includes values to indicate of at least one of: movement or gait for the human subject; or behavior data that includes values to indicate at least one of: a psychological state of the human subject or social activities performed by the human subject.

In Example 31, the subject matter of Examples 28-30 includes, evaluating the pain treatment parameters in the human subject, with the dynamic model, based on operational data obtained from use or programming of the implantable electrical neurostimulation device.

In Example 32, the subject matter of Examples 28-31 includes, the dynamic model being a continuous time model or a discrete time model, wherein the dynamic model evaluates the pain treatment parameters in the human subject over the time period based on: predicted pain of the human subject, observed pain of the human subject, dynamic model parameters, and operational data of the implantable electrical neurostimulation device.

In Example 33, the subject matter of Examples 28-32 includes, receiving, from the human subject, feedback data on the selected neurostimulation program, the feedback data received in response to deployment of the selected neurostimulation program to the human subject using the implantable electrical neurostimulation device; wherein subsequent operations using the dynamic model evaluate the feedback data as dynamic model parameters.

In Example 34, the subject matter of Examples 28-33 includes, the pain treatment parameters being stored by a data service, and wherein subsequent operations using the dynamic model obtain the pain treatment parameters from the data service and evaluate the pain treatment parameters obtained from the data service.

In Example 35, the subject matter of Examples 28-34 includes, a user interface being used to receive at least one of: at least a portion of the data related to a state of pain of the human subject, or a command to cause selection or deployment of the neurostimulation program.

In Example 36, the subject matter of Examples 28-35 includes, the selected neurostimulation program being one of a plurality of predefined neurostimulation programs available for use in the implantable electrical neurostimulation device; and wherein the dynamic model is one of a plurality of dynamic models available for identification of the pain treatment parameters, and wherein the dynamic model is selected from a dynamic model data source based on the data related to a state of pain of the human subject.

In Example 37, the subject matter of Examples 28-36 includes, the identified pain treatment parameters of the selected neurostimulation program causing a change in operation of the implantable electrical neurostimulation device, that corresponds to a change in the state of pain of the human subject; and wherein the identified pain treatment parameters of the selected neurostimulation program specifies a change in programming for the implantable electrical neurostimulation device for one or more of: pulse patterns, pulse shapes, a spatial location of pulses, waveform shapes, or a spatial location of waveform shapes, for modulated energy provided with a plurality of leads of the implantable electrical neurostimulation device.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Figure 1:
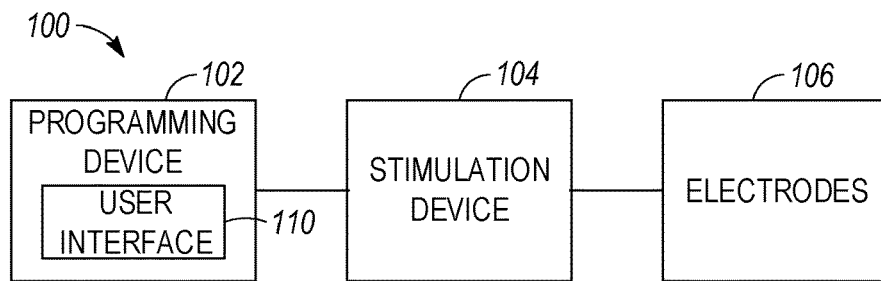
FIG. 1 illustrates, by way of example, an embodiment of a electrical neurostimulation system.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

This document discusses various techniques that can adjust programming of an implantable electrical neurostimulation device, for the treatment of chronic pain of a human subject (e.g., a patient). As an example, various systems and methods are described to identify, given a time series of pain ratings (or other pain state information), a first or second order dynamics. The dynamics are associated with a set of parameters and a set of predefined pain treatments that are analyzed in a dynamic information system. The dynamics may be re-identified at certain temporal checkpoints by the patient or a physician, to determine whether further selection, adjustment, or adaptation of the parameters are needed. Based on the identified dynamics, the dynamic information system determines a best program for each patient that is customized to a current and a predicted state of the patient, with the ultimate goal to provide improvement in the treatment of chronic pain.

Chronic pain is a common condition for many patients, but which may be addressed through the use of neurostimulation therapy (e.g., electrical spinal cord stimulation, electrical peripheral nerve stimulation, or electrical brain stimulation) to deliver treatment. One limiting factor for existing applications of neurostimulation therapies is that, even if a number of advanced programs can be applied by an electrical neurostimulation device, patients often only end up using a few of the available treatments (e.g., two or three programs). As a result, the treatment results are often not effective and the patient ends up applying programs that are not customized to the patient or a best fit for the patient. The present inventive techniques and systems improve this scenario through the use of a dynamic information system built around the patient, which is able to recommend and implement the best program that the patient should apply given his or her specific conditions, and predicted conditions.

The dynamic information system discussed herein enables the analysis of multiple aspects of relevant treatment inputs, to enable a patient, caregiver, or medical professional to select, modify, and implement certain programming parameters (e.g., settings) for a neurostimulator, based on the state of pain of the human subject. In an example, the dynamic information system applies a dynamic model, evaluating dynamic equations within a continuous time or a discrete time to evaluate system inputs including: patient pain, predicted pain, model parameters, model time, and stimulator input (e.g., programs available for use by the stimulator). The dynamic information system operates the dynamic model to provide, from the discrete-time or continuous-time evaluation, a recommendation of which the parameters are applicable to address the patient treatment of chronic pain. These programming parameters may be arranged or defined (e.g., pre-defined, modified, etc.) into sets of neurostimulation operational programs (also plainly referred to as "programs" in this document), resulting in a selection of a particular neurostimulation program that includes at least a portion of the pain treatment parameters identified as a best-fit for the human patient in the dynamic model.

The techniques of this document can enable a human subject (e.g., patient) to select, activate, modify, update, or adapt a program for a device (or to re-program a device)

within an available set of possible programs and program settings, to improve chronic pain treatment and treatment efficacy of neurostimulation device uses. In an example, programming determination logic operates within the dynamic information system to obtain data related to a state of pain of the human subject, and evaluate the state of pain to identify a measured pain level and a predicted pain level of the human subject for the chronic pain condition. The programming determination logic operates to identify pain treatment parameters using the previously described dynamic model, to evaluate the pain treatment parameters in the human subject over a time period, based on the data related to the state of pain. Finally, the programming determination logic operates to identify a program which implements the pain treatment parameters that provides a best fit for the predicted state of the patient and the patient's chronic pain state.

By way of example, operational parameters of the electrical neurostimulation device may include amplitude, frequency, duration, pulse width, pulse type, patterns of neurostimulation pulses, waveforms in the patterns of pulses, and like settings with respect to the intensity, type, and location of neurostimulator output on individual or a plurality of respective leads. The electrical neurostimulator may use current or voltage sources to provide the neurostimulator output, and apply any number of control techniques to modify the electrical simulation applied to anatomical sites or systems related to chronic pain. In various embodiments, a neurostimulator program may include parameters that define spatial, temporal, and informational characteristics for the delivery of modulated energy, including the definitions or parameters of pulses of modulated energy, waveforms of pulses, pulse blocks each including a burst of pulses, pulse trains each including a sequence of pulse blocks, train groups each including a sequence of pulse trains, and programs of such definitions or parameters, each including one or more train groups scheduled for delivery. Characteristics of the waveform that are defined in the program may include, but are not limited to the following: amplitude, pulse width, frequency, total charge injected per unit time, cycling (e.g., on/off time), pulse shape, number of phases, phase order, interphase time, charge balance, ramping, as well as spatial variance (e.g., electrode configuration changes over time). It will be understood that based on the many characteristics of the waveform itself, a program may have many parameter setting combinations that would be potentially available for use.

In various embodiments, the present subject matter may be implemented using a combination of hardware and software designed to provide users such as patients, caregivers, clinicians, researchers, physicians or others with the ability to identify, select, and implement neurostimulation programs that specifically model aspects of chronic pain in a human subject. The use of different programs may provide variation in the location, intensity, and type of defined waveforms and patterns in an effort to increase therapeutic efficacy and/or patient satisfaction for neurostimulation therapies, including but not being limited to SCS and DBS therapies. While neurostimulation is specifically discussed as an example, the present subject matter may apply to any therapy that employs stimulation pulses of electrical or other forms of energy for treating chronic pain.

The delivery of neurostimulation energy that is discussed herein may be delivered in the form of electrical neurostimulation pulses. The delivery is controlled using stimulation parameters that specify spatial (where to stimulate), temporal (when to stimulate), and informational (patterns of pulses directing the nervous system to respond as desired) aspects of a pattern of neurostimulation pulses. Many current neurostimulation systems are programmed to deliver periodic pulses with one or a few uniform waveforms continuously or in bursts. However, neural signals may include more sophisticated patterns to communicate various types of information, including sensations of pain, pressure, temperature, etc. Accordingly, the following drawings provide an introduction to the features of an example neurostimulation system and how such programming may be accomplished through neurostimulation systems.

FIG. 1 illustrates an embodiment of an electrical neurostimulation system 100.

System 100 includes electrodes 106, a stimulation device 104, and a programming device 102. Electrodes 106 are configured to be placed on or near one or more neural targets in a patient. Stimulation device 104 is configured to be electrically connected to electrodes 106 and deliver neurostimulation energy, such as in the form of electrical pulses, to the one or more neural targets though electrodes 106. The delivery of the neurostimulation is controlled by using a plurality of stimulation parameters, such as stimulation parameters specifying a pattern of the electrical pulses and a selection of electrodes through which each of the electrical pulses is delivered. In various embodiments, at least some parameters of the plurality of stimulation parameters are programmable by a clinical user, such as a physician or other caregiver who treats the patient using system 100. Programming device 102 provides the user with accessibility to the user-programmable parameters. In various embodiments, programming device 102 is configured to be communicatively coupled to stimulation device 104 via a wired or wireless link.

In various embodiments, programming device 102 includes a user interface 110 (e.g., a user interface embodied by a graphical, text, voice, or hardware-based user interface) that allows the user to set and/or adjust values of the user-programmable parameters by creating, editing, loading, and removing programs that include parameter combinations such as patterns and waveforms. These adjustments may also include changing and editing values for the user-programmable parameters or sets of the user-programmable parameters individually (including values set in response to a therapy efficacy indication). Such waveforms may include, for example, the waveform of a pattern of neurostimulation pulses to be delivered to the patient as well as individual waveforms that are used as building blocks of the pattern of neurostimulation pulses. Examples of such individual waveforms include pulses, pulse groups, and groups of pulse groups. The program and respective sets of parameters may also define an electrode selection specific to each individually defined waveform.

As described in more detail below with respect to FIGS. 7 to 9, a user, e.g., the patient, or a clinician or other medical professional associated with the patient can select, load, modify, and implement one or more parameters of a defined program for neurostimulation treatment, based on programming determination logic that identifies the defined program using a dynamic model. Based on a modeling of pain, the programming determination logic can determine which program is likely to produce an improvement for a predetermined condition involving chronic pain. Example parameters that can be implemented by a selected program include, but are not limited to the following: amplitude, pulse width, frequency, duration, total charge injected per unit time, cycling (e.g., on/off time), pulse shape, number of phases, phase order, interphase time, charge balance, ramping, as well as spatial variance (e.g., electrode configuration changes over time).

Figure 6:
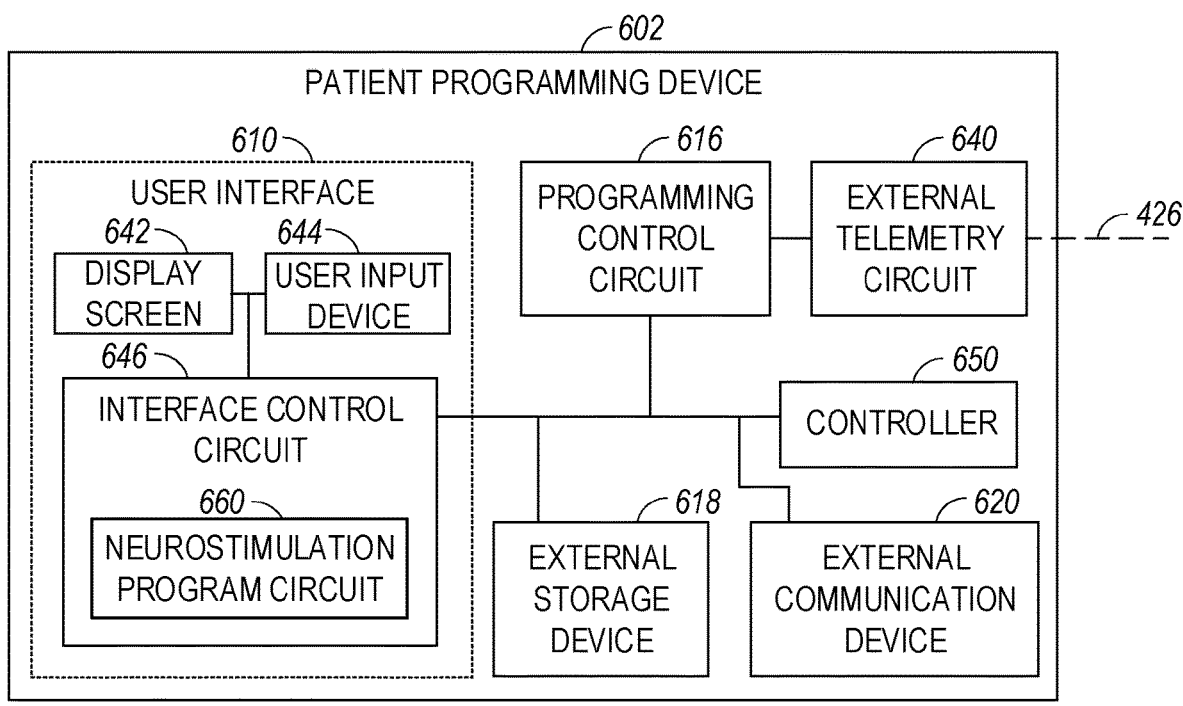
FIG. 6 illustrates, by way of example, an embodiment of a patient programming device for a neurostimulation system, such as the implantable electrical neurostimulation system of FIG. 4.

As detailed in FIG. 6, a controller, e.g., controller 650 of FIG. 6, can implement program(s) and parameter setting(s) to implement a specific neurostimulation waveform, pattern, or energy output, using a program or setting in storage, e.g., external storage device 618 of FIG. 6, or using settings communicated via an external communication device 620 of FIG. 6 corresponding to the selected program. The implementation of such program(s) or setting(s) may further define a therapy strength and treatment type corresponding to a specific pulse group, or a specific group of pulse groups, based on the specific program(s) or setting(s). As also described in more detail below with respect to FIG. 7 and thereafter, a program modeling system and program determination logic (operating as an implementation of a dynamic information system) may operate to produce this information based on operation of the presently described dynamic model. As also described, a clinician or the patient may also affect use and implementation of such programs or settings, including in settings where a combination of dynamic and manual control are involved.

Portions of the stimulation device 104, e.g., implantable medical device, or the programming device 102 can be implemented using hardware, software, or any combination of hardware and software. Portions of the stimulation device 104 or the programming device 102 may be implemented using an application-specific circuit that can be constructed or configured to perform one or more particular functions, or can be implemented using a general-purpose circuit that can be programmed or otherwise configured to perform one or more particular functions. Such a general-purpose circuit can include a microprocessor or a portion thereof, a microcontroller or a portion thereof, or a programmable logic circuit, or a portion thereof. The system 100 could also include a subcutaneous medical device (e.g., subcutaneous ICD, subcutaneous diagnostic device), wearable medical devices (e.g., patch based sensing device), or other external medical devices.

Figure 2:
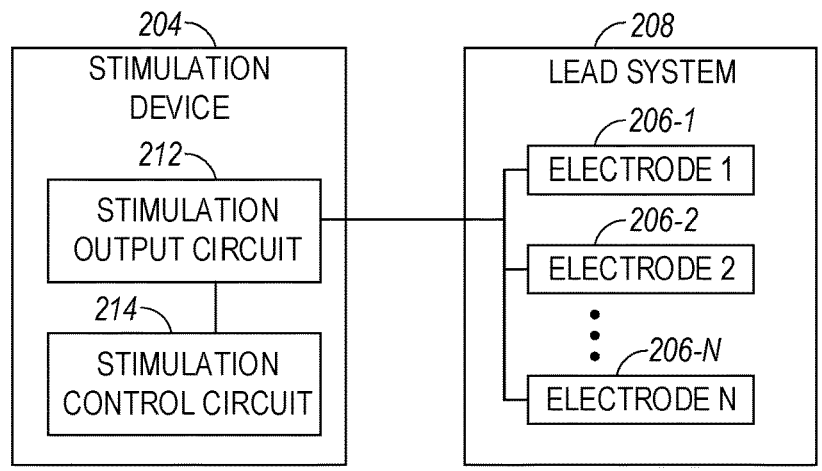
FIG. 2 illustrates, by way of example, an embodiment of a stimulation device and a lead system, such as may be implemented in the electrical neurostimulation system of FIG. 1.

FIG. 2 illustrates an embodiment of a stimulation device 204 and a lead system 208, such as may be implemented in neurostimulation system 100 of FIG. 1. Stimulation device 204 represents an embodiment of stimulation device 104 and includes a stimulation output circuit 212 and a stimulation control circuit 214. Stimulation output circuit 212 produces and delivers neurostimulation pulses, including the neurostimulation waveform and parameter settings implemented via a program selected or implemented with the user interface 110. Stimulation control circuit 214 controls the delivery of the neurostimulation pulses using the plurality of stimulation parameters, which specifies a pattern of the neurostimulation pulses. Lead system 208 includes one or more leads each configured to be electrically connected to stimulation device 204 and a plurality of electrodes 206 distributed in the one or more leads. The plurality of electrodes 206 includes electrode 206-1, electrode 206-2, . . . . electrode 206-N, each a single electrically conductive contact providing for an electrical interface between stimulation output circuit 212 and tissue of the patient, where N≥2. The neurostimulation pulses are each delivered from stimulation output circuit 212 through a set of electrodes selected from electrodes 206. In various embodiments, the neurostimulation pulses may include one or more individually defined pulses, and the set of electrodes may be individually definable by the user for each of the individually defined pulses.

In various embodiments, the number of leads and the number of electrodes on each lead depend on, for example, the distribution of target(s) of the neurostimulation and the need for controlling the distribution of electric field at each target. In one embodiment, lead system 208 includes 2 leads each having 8 electrodes. Those of ordinary skill in the art will understand that the neurostimulation system 100 may include additional components such as sensing circuitry for patient monitoring and/or feedback control of the therapy, telemetry circuitry, and power.

The neurostimulation system may be configured to modulate spinal target tissue or other neural tissue. The configuration of electrodes used to deliver electrical pulses to the targeted tissue constitutes an electrode configuration, with the electrodes capable of being selectively programmed to act as anodes (positive), cathodes (negative), or left off (zero). In other words, an electrode configuration represents the polarity being positive, negative, or zero. Other parameters that may be controlled or varied include the amplitude, pulse width, and rate (or frequency) of the electrical pulses. Each electrode configuration, along with the electrical pulse parameters, can be referred to as a "modulation parameter" set. Each set of modulation parameters, including fractionalized current distribution to the electrodes (as percentage cathodic current, percentage anodic current, or off), may be stored and combined into a program that can then be used to modulate multiple regions within the patient.

The neurostimulation system may be configured to deliver different electrical fields to achieve a temporal summation of modulation. The electrical fields can be generated respectively on a pulse-by-pulse basis. For example, a first electrical field can be generated by the electrodes (using a first current fractionalization) during a first electrical pulse of the pulsed waveform, a second different electrical field can be generated by the electrodes (using a second different current fractionalization) during a second electrical pulse of the pulsed waveform, a third different electrical field can be generated by the electrodes (using a third different current fractionalization) during a third electrical pulse of the pulsed waveform, a fourth different electrical field can be generated by the electrodes (using a fourth different current fractionalized) during a fourth electrical pulse of the pulsed waveform, and so forth. These electrical fields can be rotated or cycled through multiple times under a timing scheme, where each field is implemented using a timing channel. The electrical fields may be generated at a continuous pulse rate, or as bursts of pulses. Furthermore, the interpulse interval (i.e., the time between adjacent pulses), pulse amplitude, and pulse duration during the electrical field cycles may be uniform or may vary within the electrical field cycle. Some examples are configured to determine a modulation parameter set to create a field shape to provide a broad and uniform modulation field such as may be useful to prime targeted neural tissue with sub-perception modulation. Some examples are configured to determine a modulation parameter set to create a field shape to reduce or minimize modulation of non-targeted tissue (e.g., dorsal column tissue). Various examples disclosed herein are directed to shaping the modulation field to enhance modulation of some neural structures and diminish modulation at other neural structures. The modulation field may be shaped by using multiple independent current control (MICC) or multiple independent voltage control to guide the estimate of current fractionalization among multiple electrodes and estimate a total amplitude that provide a desired strength. For example, the modulation field may be shaped to enhance the modulation of dorsal horn neural tissue and to minimize the modulation of dorsal column tissue. A benefit of MICC is that MICC accounts for various in electrode-tissue coupling efficiency and perception threshold at each individual contact, so that "hotspot" stimulation is eliminated.

The number of electrodes available combined with the ability to generate a variety of complex electrical pulses, presents a huge selection of available modulation parameter sets to the clinician or patient. For example, if the neurostimulation system to be programmed has sixteen electrodes, millions of modulation parameter value combinations may be available for programming into the neurostimulation system. Furthermore, SCS systems may have as many as thirty-two electrodes, which exponentially increases the number of modulation parameter value combinations available for programming. To facilitate such programming, a clinician often initially programs and modifies the modulation parameters through a computerized programming system, to allow the modulation parameters to be established from starting parameter sets (programs) and patient and clinician feedback. In addition, the patient often is provided with a limited set of controls to switch from a first program to a second program, based on user preferences and the subjective amount of pain or discomfort that the patient is treating. However, the implementation and use of a program modeling system and program determination logic as described further in FIGS. 7 to 9 and thereafter provides a mechanism for optimized adjustment and modifications to implemented parameter settings, in a fashion that emphasizes chronic pain improvement from a different program on the neurostimulator deployment.

Figure 3:
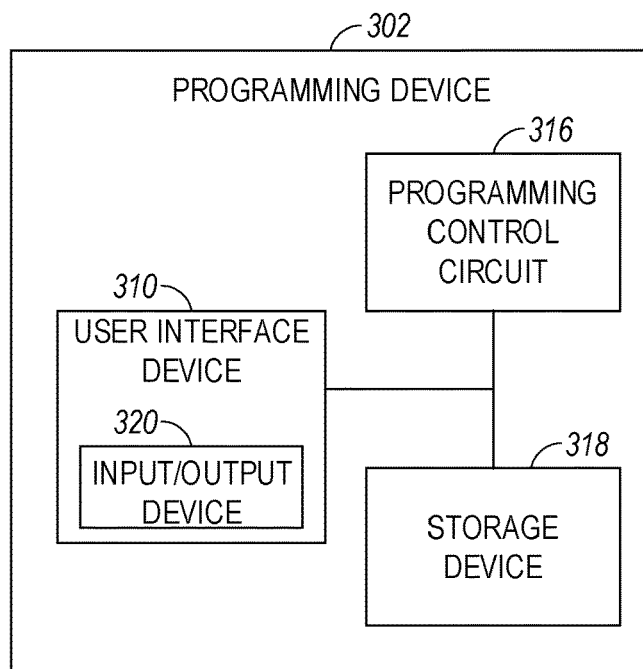
FIG. 3 illustrates, by way of example, an embodiment of a programming device, such as may be implemented in the neurostimulation system of FIG. 1.

FIG. 3 illustrates an embodiment of a programming device 302, such as may be implemented in neurostimulation system 100. Programming device 302 represents an embodiment of programming device 102 and includes a storage device 318, a programming control circuit 316, and a user interface device 310. Programming control circuit 316 generates the plurality of stimulation parameters that controls the delivery of the neurostimulation pulses according to the pattern of the neurostimulation pulses. The user interface device 310 represents an embodiment to implement the user interface 110.

In various embodiments, the user interface device 310 includes an input/output device 320 that is capable to receive user interaction and commands to load, modify, and implement neurostimulation programs and schedule delivery of the neurostimulation programs. In various embodiments, the input/output device 320 allows the user to create, establish, access, and implement respective parameter values of a neurostimulation program through graphical selection (e.g., in a graphical user interface output with the input/output device 320), including values of a therapeutic neurostimulation field. In some examples, the user interface device 310 can receive user input to initiate the implementation of the programs which are recommended, modified, selected, or loaded through use of a program modeling system, which are described in more detail below.

In various embodiments, the input/output device 320 allows the patient user to apply, change, modify, or discontinue certain building blocks of a program and a frequency at which a selected program is delivered. In various embodiments, the input/output device 320 can allow the patient user to save, retrieve, and modify programs (and program settings) loaded from a clinical encounter, managed from a patient control computing device, or stored in storage device 318 as templates. In various embodiments, the input/output device 320 and accompanying software on the user interface device 310 allows newly created building blocks, program components, programs, and program modifications to be saved, stored, or otherwise persisted in storage device 318.

In one embodiment, the input/output device 320 includes a touchscreen. In various embodiments, the input/output device 320 includes any type of presentation device, such as interactive or non-interactive screens, and any type of user input device that allows the user to interact with a user interface to implement, remove, or schedule the programs, and as applicable, to edit or modify waveforms, building blocks, and program components. Thus, the input/output device 320 may include one or more of a touchscreen, keyboard, keypad, touchpad, trackball, joystick, and mouse. In various embodiments, circuits of the neurostimulation system 100, including its various embodiments discussed in this document, may be implemented using a combination of hardware and software. For example, the logic of the user interface 110, the stimulation control circuit 214, and the programming control circuit 316, including their various embodiments discussed in this document, may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 4:
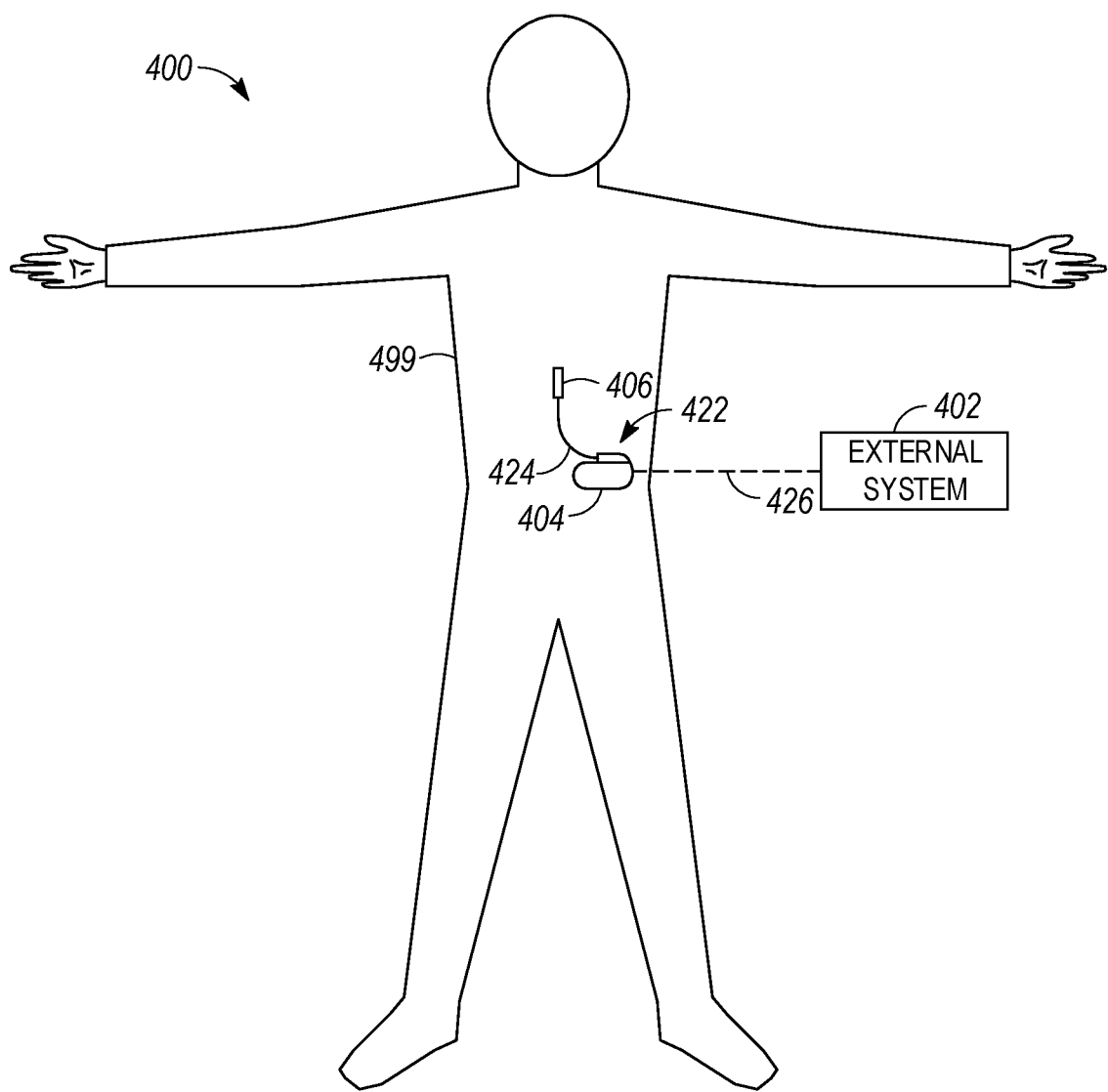
FIG. 4 illustrates, by way of example, an implantable electrical neurostimulation system and portions of an environment in which the system may be used.

FIG. 4 illustrates an implantable electrical neurostimulation system 400 and portions of an environment in which system 400 may be used. System 400 includes an implantable system 422, an external system 402, and a telemetry link 426 providing for wireless communication between an implantable system 422 and an external system 402. Implantable system 422 is illustrated in FIG. 4 as being implanted in the patient's body 499. The system is illustrated for implantation near the spinal cord. However, the neuromodulation system may be configured to modulate other neural targets.

Implantable system 422 includes an implantable stimulator 404 (also referred to as an implantable pulse generator, or IPG), a lead system 424, and electrodes 406, which represent an embodiment of the stimulation device 204, the lead system 208, and the electrodes 206, respectively. The external system 402 represents an embodiment of the programming device 302.

In various embodiments, the external system 402 includes one or more external (non-implantable) devices each allowing the user and/or the patient to communicate with the implantable system 422. In some embodiments, the external system 402 includes a programming device intended for the user to initialize and adjust settings for the implantable stimulator 404 and a remote control device intended for use by the patient. For example, the remote control device may allow the patient to turn the implantable stimulator 404 on and off and/or adjust certain patient-programmable parameters of the plurality of stimulation parameters. The remote control device may also provide a mechanism to receive and process feedback on the operation of the implantable neuromodulation system. Feedback may include metrics or an efficacy indication reflecting perceived pain, effectiveness of therapies, or other aspects of patient comfort or condition. Such feedback may be automatically detected from a patient's physiological state, or manually obtained from user input entered in a user interface.

For the purposes of this specification, the terms "neurostimulator," "stimulator," "neurostimulation," and "stimulation" generally refer to the delivery of electrical energy that affects the neuronal activity of neural tissue, which may be excitatory or inhibitory; for example by initiating an action potential, inhibiting or blocking the propagation of action potentials, affecting changes in neurotransmitter/neuromodulator release or uptake, and inducing changes in neuroplasticity or neurogenesis of tissue. It will be understood that other clinical effects and physiological mechanisms may also be provided through use of such stimulation techniques.

Figure 5:
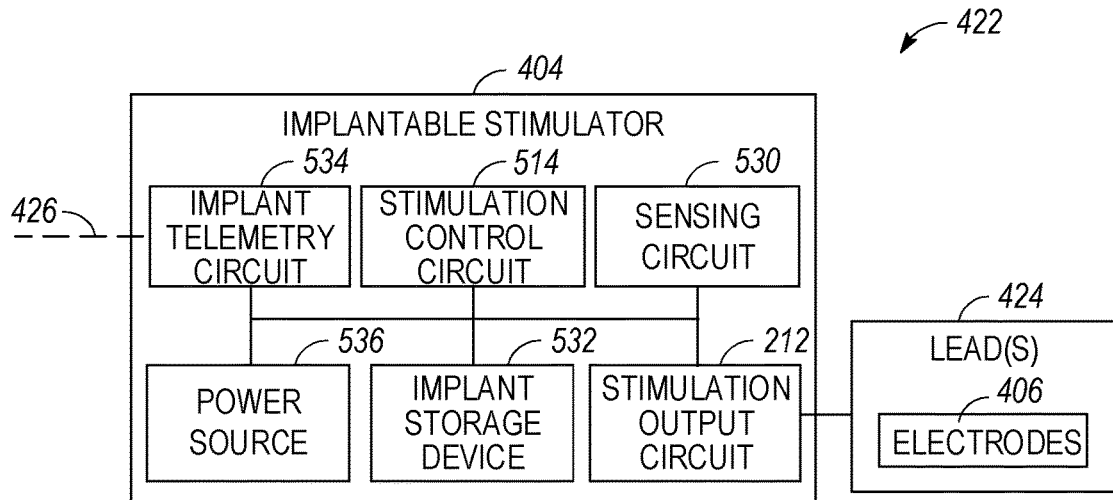
FIG. 5 illustrates, by way of example, an embodiment of an implantable electrical stimulator and one or more leads of a neurostimulation system, such as the implantable electrical neurostimulation system of FIG. 4.

FIG. 5 illustrates an embodiment of the implantable stimulator 404 and the one or more leads 424 of an implantable neurostimulation system, such as the implantable system 422. The implantable stimulator 404 may include a sensing circuit 530 that is optional and required only when the stimulator has a sensing capability, stimulation output circuit 212, a stimulation control circuit 514, an implant storage device 532, an implant telemetry circuit 534, and a power source 536. The sensing circuit 530, when included and needed, senses one or more physiological signals for purposes of patient monitoring and/or feedback control of the neurostimulation. Examples of the one or more physiological signals includes neural and other signals each indicative of a condition of the patient that is treated by the neurostimulation and/or a response of the patient to the delivery of the neurostimulation.

The stimulation output circuit 212 is electrically connected to electrodes 406 through the one or more leads 424, and delivers each of the neurostimulation pulses through a set of electrodes selected from the electrodes 406. The stimulation output circuit 212 can implement, for example, the generating and delivery of a customized neurostimulation waveform (e.g., implemented from a parameter of a program selected with the present dynamic model or dynamical information system) to an anatomical target of a patient.

The stimulation control circuit 514 represents an embodiment of the stimulation control circuit 214 and controls the delivery of the neurostimulation pulses using the plurality of stimulation parameters specifying the pattern of the neurostimulation pulses. In one embodiment, the stimulation control circuit 514 controls the delivery of the neurostimulation pulses using the one or more sensed physiological signals and processed input from patient feedback interfaces. The implant telemetry circuit 534 provides the implantable stimulator 404 with wireless communication with another device such as a device of the external system 402, including receiving values of the plurality of stimulation parameters from the external system 402. The implant storage device 532 stores values of the plurality of stimulation parameters, including parameters from one or more programs obtained using the patient feedback and the programming modification logic techniques disclosed herein.

The power source 536 provides the implantable stimulator 404 with energy for its operation. In one embodiment, the power source 536 includes a battery. In one embodiment, the power source 536 includes a rechargeable battery and a battery charging circuit for charging the rechargeable battery. The implant telemetry circuit 534 may also function as a power receiver that receives power transmitted from external system 402 through an inductive couple.

In various embodiments, the sensing circuit 530 (if included), the stimulation output circuit 212, the stimulation control circuit 514, the implant telemetry circuit 534, the implant storage device 532, and the power source 536 are encapsulated in a hermetically sealed implantable housing. In various embodiments, the lead(s) 424 are implanted such that the electrodes 406 are placed on and/or around one or more targets to which the neurostimulation pulses are to be delivered, while the implantable stimulator 404 is subcutaneously implanted and connected to the lead(s) 424 at the time of implantation.

FIG. 6 illustrates an embodiment of an external patient programming device 602 of an implantable neurostimulation system, such as the external system 402, with the external patient programming device 602 illustrated to receive commands (e.g., program selections, information) directly or indirectly from a dynamical information system and the dynamic models (not shown in FIG. 6, but discussed with reference to FIGS. 7 to 9, below). The external patient programming device 602 represents an embodiment of the programming device 302, and includes an external telemetry circuit 640, an external storage device 618, a programming control circuit 616, a user interface device 610, a controller 650, and an external communication device 620.

The external telemetry circuit 640 provides the external patient programming device 602 with wireless communication to and from another controllable device such as the implantable stimulator 404 via the telemetry link 426, including transmitting one or a plurality of stimulation parameters (including changed stimulation parameters of a selected program) to the implantable stimulator 404. In one embodiment, the external telemetry circuit 640 also transmits power to the implantable stimulator 404 through inductive coupling.

The external communication device 620 provides a mechanism to conduct communications with a programming information source, such as a data service, program modeling system, or other aspects of a dynamic information system, to receive program information via an external communication link (not shown). As described in the following paragraphs, the program modeling system may be used to identify a program or program data to the external patient programming device 602 that corresponds to a new or different neurostimulation program or characteristics of a neurostimulation program (which is, in turn, selected to provide an improved treatment of a chronic pain condition by the dynamic model). The external communication device 620 and the programming information source may communicate using any number of wired or wireless communication mechanisms described in this document, including but not limited to an IEEE 802.11 (Wi-Fi), Bluetooth, Infrared, and like standardized and proprietary wireless communications implementations. Although the external telemetry circuit 640 and the external communication device 620 are depicted as separate components within the external patient programming device 602, the functionality of both of these components may be integrated into a single communication chipset, circuitry, or device.

The external storage device 618 stores a plurality of existing neurostimulation waveforms, including definable waveforms for use as a portion of the pattern of the neurostimulation pulses, settings and setting values, other portions of a program, and related treatment efficacy indication values. In various embodiments, each waveform of the plurality of individually definable waveforms includes one or more pulses of the neurostimulation pulses, and may include one or more other waveforms of the plurality of individually definable waveforms. Examples of such waveforms include pulses, pulse blocks, pulse trains, and train groupings, and programs. The existing waveforms stored in the external storage device 618 can be definable at least in part by one or more parameters including, but not limited to the following: amplitude, pulse width, frequency, duration(s), electrode configurations, total charge injected per unit time, cycling (e.g., on/off time), waveform shapes, spatial locations of waveform shapes, pulse shapes, number of phases, phase order, interphase time, charge balance, and ramping.

The external storage device 618 also stores a plurality of individually definable fields that may be implemented as part of a program. Each waveform of the plurality of individually definable waveforms is associated with one or more fields of the plurality of individually definable fields. Each field of the plurality of individually definable fields is defined by one or more electrodes of the plurality of electrodes through which a pulse of the neurostimulation pulses is delivered and a current distribution of the pulse over the one or more electrodes. A variety of settings in a program (including settings changed as a result of evaluation with the dynamical information system and the dynamic models) may be correlated to the control of these waveforms and definable fields.

The programming control circuit 616 represents an embodiment of a programming control circuit 316 and generates the plurality of stimulation parameters, which is to be transmitted to the implantable stimulator 404, based on the pattern of the neurostimulation pulses. The pattern is defined using one or more waveforms selected from the plurality of individually definable waveforms (e.g., defined by a program) stored in an external storage device 618. In various embodiments, a programming control circuit 616 checks values of the plurality of stimulation parameters against safety rules to limit these values within constraints of the safety rules. In one embodiment, the safety rules are heuristic rules.

The user interface device 610 represents an embodiment of the user interface device 310 and allows the user (including a patient or clinician) to select, modify, enable, disable, activate, schedule, or otherwise define a program or sets of programs for use with the neurostimulation device and perform various other monitoring and programming tasks for operation of the neurostimulation device. The user interface device 610 can enable a user to implement, save, persist, or update a program including the program or program parameters recommended or indicated by the programming information source, such as a data service or program modeling system. The user interface device 610 includes a display screen 642, a user input device 644, and an interface control circuit 646. The display screen 642 may include any type of interactive or non-interactive screens, and the user input device 644 may include any type of user input devices that supports the various functions discussed in this document, such as a touchscreen, keyboard, keypad, touchpad, trackball, joystick, and mouse. The user interface device 610 may also allow the user to perform any other functions discussed in this document where user interface input is suitable.

Interface control circuit 646 controls the operation of the user interface device 610 including responding to various inputs received by the user input device 644 that define or modify characteristics of implementation (including conditions, schedules, and variations) of one or more programs, parameters within the program, characteristics of one or more stimulation waveforms within a program, and like neurostimulator operational values that may be entered or selected with the external patient programming device 602, or obtained from the programming information source, such as the data service, or the program modeling system. Interface control circuit 646 includes a neurostimulation program circuit 660 that may generate a visualization of such characteristics of implementation, and receive and implement commands to implement the program and the neurostimulator operational values (including a status of implementation for such operational values). These commands and visualization may be performed in a review and guidance mode, status mode, or in a real-time programming mode.

The controller 650 can be a microprocessor that communicates with the external telemetry circuit 640, the external communication device 620, the external storage device 618, the programming control circuit 616, and the user interface device 610, via a bidirectional data bus. The controller 650 can be implemented by other types of logic circuitry (e.g., discrete components or programmable logic arrays) using a state machine type of design. As used in this disclosure, the term "circuitry" should be taken to refer to either discrete logic circuitry, firmware, or to the programming of a microprocessor.

As will be understood, the variety of settings for a neurostimulation device may be provided by many variations of programming parameter settings within programs. Existing patient programmers only provide a limited ability for a patient to cycle through programs that have defined programming parameters, with hundreds or thousands of specific settings often being rolled up into a single program. The following system and methods provide technical mechanisms to recommend and adjust such programs and parameters for chronic pain therapy in response to operation of a dynamical model. This dynamical model may operate to explore a prediction or recommendation of a program, based on factors such as user decisions, feedback on applied programs, pain level observations, and the like. The dynamical model may provide modifications to one or more settings in a program, selections of new or different programs, recommended or suggested adjustments or modifications to an existing program, and like variations.

In an example, a dynamical model may be implemented in continuous time or discrete time, as modeled with the following equations:

$\hat{x}$ := patient pain
x := predicted pain
θ := model parameters
t := model time
u(•) := stimulator input, $u(•) \in \{u_1, \ldots, u_m\}$
m := number of available programs from the stimulator $$\dot{x}(t) = f_c(t, x, \theta, \hat{x}, u(\bullet)) \text{ (continuous time model)}$$

$$x(t+1) = f_d(t, x, \theta, \hat{x}, u(\bullet)) \text{ (discrete time model)} \qquad \text{EQUATION 1}$$

In an example, operation of a discrete time model may be represented by the following equation, where $T_w$ is a time window, and Θ are admissible parameters:

$$\theta(t) := \arg\min_\theta \left( \sum_{k=t-T_w}^{t} |x(k) - \hat{x}(k)|^2 \right), \text{ s.t. } \theta \in \Theta \qquad \text{EQUATION 2}$$

In an example, operation of a continuous time model may be represented by the following equation, where $T_w$ is a time window, and Θ are admissible parameters:

$$\theta(t) := \arg\min_\theta \left( \int_{t-T_w}^{t} |x(\tau) - \hat{x}(\tau)|^2 d\tau \right), \text{ s.t. } \theta \in \Theta \qquad \text{EQUATION 3}$$

In an example, the following equation illustrates a discrete-time dynamical system with identified parameters and additive noise:

$$u(t) := \arg\min_{u \in \{u_1,\ldots,u_m\}} \sum_{t=t}^{t+T_c} J(x, u), \text{ s.t.} \quad \text{EQUATION 4}$$

In an example, the following equation illustrates a continuous-time dynamical system with identified parameters and additive noise:

$$u(t) := \arg\min_{u \in \{u_1,\ldots,u_m\}} \int_{t=t}^{t+T_c} J(x, u)d\tau, \text{ s.t.} \quad \text{EQUATION 5}$$

With implementation of these dynamical equations, a control system may operate a predictive control-like algorithm that adapts to future use cases based on prior activities and the universe of available settings and programs to use. Further, this control system is adaptive in the sense that the model may be "trained" over time based on prior operations and how a patient directly responds to the changes in programming. Accordingly, with suitable patient and medical professional oversight and guidance, a neurostimulation program may be optimized for treatment of chronic pain using the presently disclosed dynamical models.

The following drawings illustrate example implementations of systems utilizing these or similar dynamical models for the purpose of chronic pain treatment. It will be understood that variations to the parameters and dynamic equations listed above, as used for the treatment of chronic pain with neurostimulation programs, are within the scope of the present disclosure.

Figure 7:
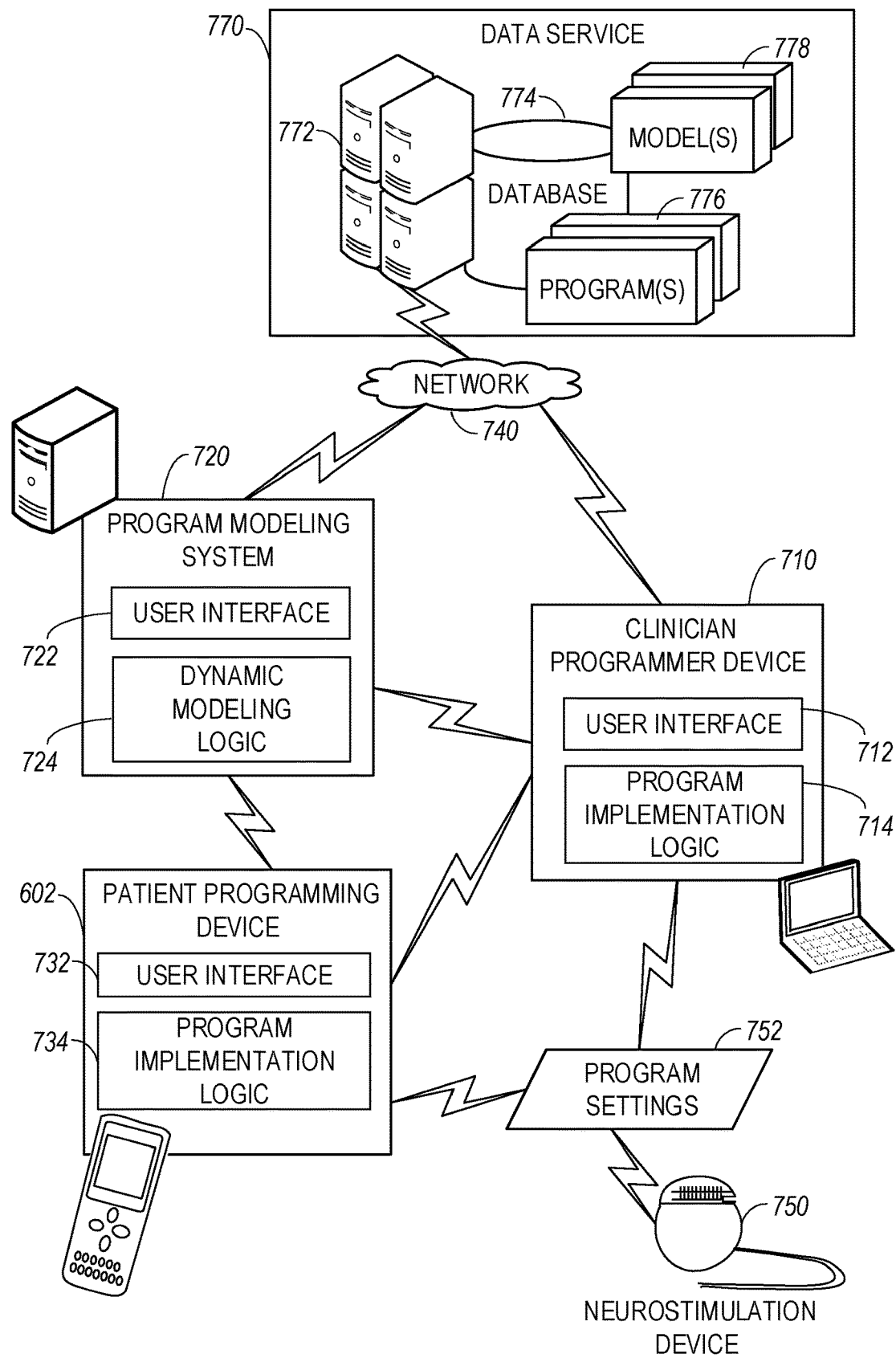
FIG. 7 illustrates, by way of example, an embodiment of data interactions among a clinician programmer device, a patient programming device, a program modeling system, and a programming data service for providing and implementing respective programs of defined parameter settings for operation of an electrical neurostimulation device.

FIG. 7 illustrates, by way of example, an embodiment of data interactions among a clinician programmer device 710, a program modeling system 720, an external patient programming device 602, and a programming data service 770 for providing and modifying respective programs of defined parameter settings of a neurostimulation device, in connection with dynamic models of chronic pain treatments. The program modeling system 720 is shown in FIG. 7 in the form of a computing device (e.g., a server) with the computing device being specially programmed to communicate over a network the results of the dynamic modeling logic 724 (e.g., with an algorithm implemented in software that is executed on the computing device). The program modeling system 720 may also include a user interface 722 (e.g., in a software app interface, or an application programming interface) which provides the similar results to another system or to a human user. It will be understood that other form factors and embodiments of the program modeling system 720, including in the integration of other programming devices, data services, or information services, may also be deployed.

The program modeling system 720 and the clinician programmer device 710 may communicate to a programming data service 770 via a network 740 (e.g., a private local area network, public wide area network, the Internet, and the like) to obtain programs, program settings, program modifications, recommendations, or like information related to programming (programs) or modeling (e.g., models). The programming data service 770 serves as a data service to host program information for a plurality of neurostimulation programs (e.g., across multiple patients, facilities, or facility locations). In an example, the programming data service 770 may be operated or hosted by a research institution, medical service provider, or a medical device provider (e.g., a manufacturer of the neurostimulation device) for managing data and settings for respective programs 776 and models 778 among a plurality of clinical deployments. The programming data service 770 may provide an interface to backend data components such as a data processing server 772 and a database 774, to provide a plurality of programs 776 and models 778 and related settings. For instance, the programming data service 770 may be accessed using an application programming interface (API) or other remotely accessible interface accessible via the network 740.

In an example, the program settings 752 to update the parameter(s) or program(s) of the neurostimulation device 750 are first selected by the program modeling system 720, and then communicated to the neurostimulation device 750 by the external patient programming device 602. In another example, the dynamic modeling logic 724 results in selection (and potentially, creation) of an entirely new program, or a customized program, which may be communicated in the program settings 752. The clinician programmer device 710 can operate in a similar fashion, with use of a user interface 712 and program implementation logic 714 to select, define, edit, and modify parameter(s) or program(s) in a clinical setting through use of the program modeling system. Finally, in some examples, the program settings 752 may be directly communicated from the clinician programmer device 710 rather than a patient programming device 602.

The external patient programming device 602 is illustrated in the form factor of a patient-operable remote control, but may be embodied in a number of other form factors. The external patient programming device 602 operates to communicate program data to the neurostimulation device 750 through use of program implementation logic 734 and a user interface 732 (e.g., a user interface provided by the user interface device 610 discussed in FIG. 6). In an example, a neurostimulation program selection is transmitted to the external patient programming device 602 (or clinician programmer device 710) from the program modeling system 720, and is processed by the program implementation logic 734 (or program implementation logic 714) to determine an appropriate operational change to the neurostimulation device 750.

Figure 8:
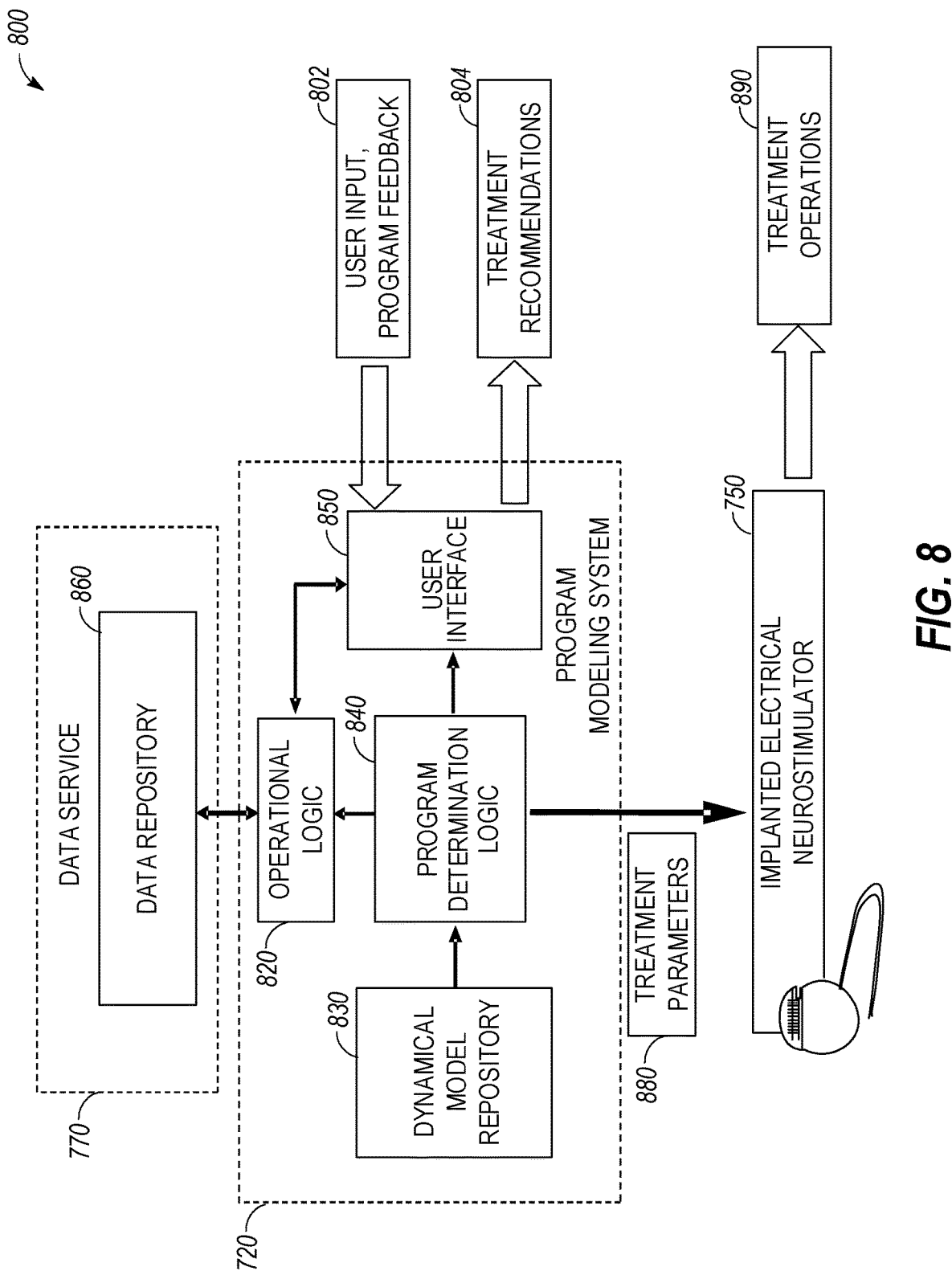
FIG. 8 illustrates, by way of example, an embodiment of a program modeling system adapted for identifying programming parameters of an electrical neurostimulation treatment.

FIG. 8 illustrates, by way of example, a block diagram 800 of an embodiment of the program modeling system 720 adapted for identifying programming parameters of a neurostimulation treatment. As shown, the block diagram 800 illustrates data flows among the data service 770, the program modeling system, and the neurostimulation device 750, as a result of program determination logic 840 which effects an appropriate program selection using dynamic models. It will be understood that additional features and data flows may occur in connection with the use of the program determination logic 840 and the dynamic models described herein.

The program modeling system 720 is depicted as receiving user input and program feedback 802, for use in determining operative values in the dynamic model. In an example, this user input and program feedback 802 is received in a user interface 850 (e.g., a graphical user interface, an application programming interface, etc.). The user interface 850 may also receive additional settings (not shown), constraints, and conditions for operation and use of a dynamic model.

The program modeling system 720 is also depicted as outputting treatment recommendations 804, for user control (e.g., by a patient, a clinician, a caregiver, etc.). These treatment recommendations 804 may include a set of suggested programs as determined by the dynamic model.

The program modeling system 720 performs coordination of these operations, and the execution of one or more dynamic models (and associated dynamic equation algorithms) through the user of operational logic 820 that coordinates with the program determination logic 840. In an example, the operational logic 820 interfaces with a data repository 860 to access and obtain historical data relevant to the dynamic model, programs, pain information, or other aspects relevant to neurostimulation treatment or the program modeling.

The program modeling system 720 also coordinates the selection of a dynamic model for use in program modeling from a dynamical model repository 830. In an example, the program determination logic 840 evaluates the user input and program feedback 802, and identifies relevant programs, dynamical models, and dynamical model data parameters (e.g., from data repository 860 and dynamical model repository 830) for evaluation in a dynamical model. The program modeling system 720 then provides treatment recommendations 804 (e.g., through the user interface 850), or the selection of relevant treatment parameters 880, for control of the neurostimulation device 750. The operation of the neurostimulation device 750 with the selected program and parameters results in treatment operations 890 for chronic pain relief.

Figure 9:
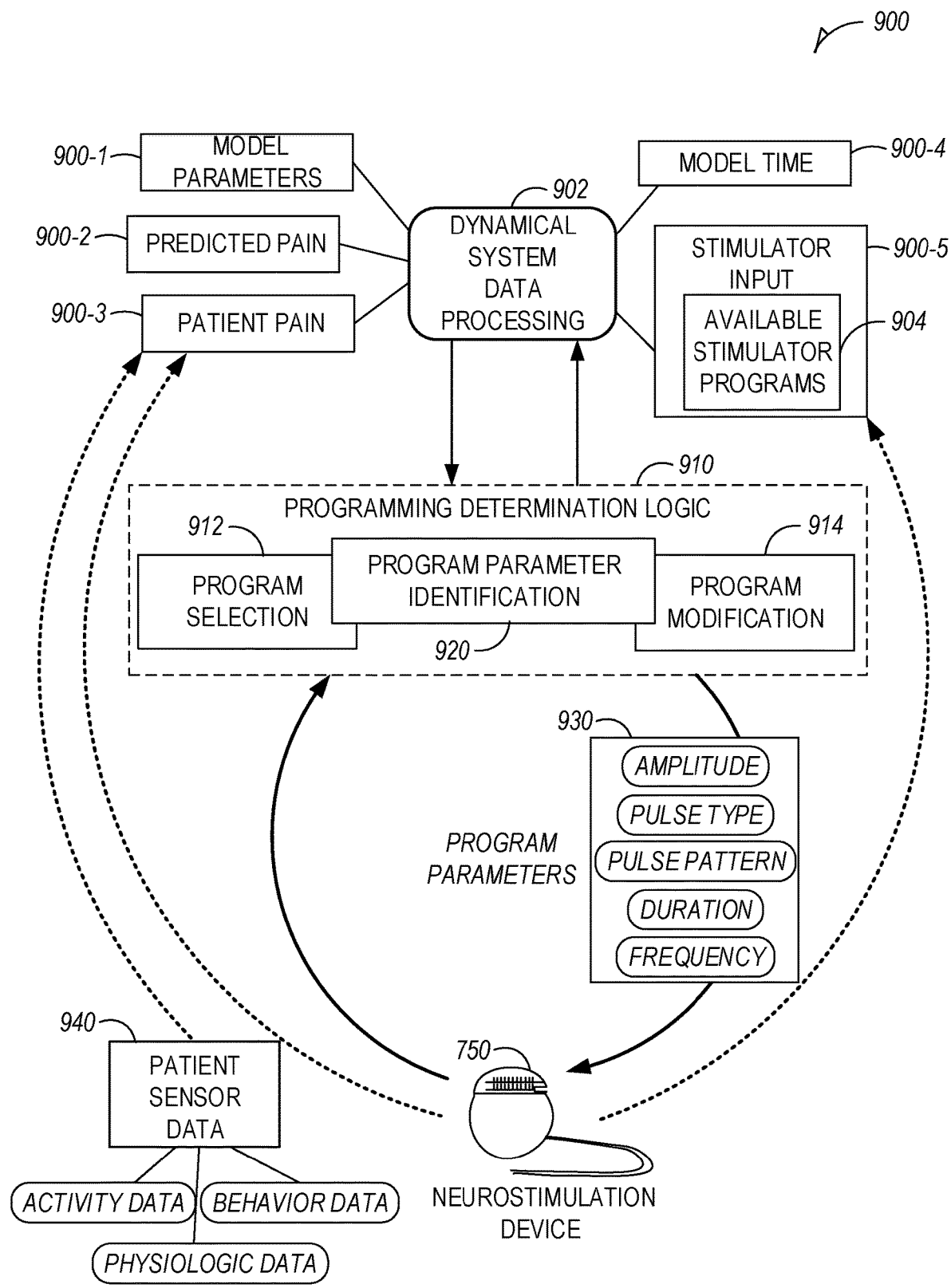
FIG. 9 illustrates, by way of example, an embodiment of a data and control flow between a dynamical system data processing model and programming determination logic, used to communicate and modify programming parameters of an electrical neurostimulation treatment.

FIG. 9 illustrates, by way of example, an embodiment of a data and control flow between a dynamical system data processing model 902 and programming determination logic 910, used to communicate and modify programming parameters 930 of a neurostimulation treatment (e.g., implemented for the neurostimulation device 750). As illustrated, the data and control flow may include a plurality of inputs 900 that are provided as part of a dynamic system data processing 902, which may implement a dynamic model (e.g., in the form of an algorithm including the dynamic equations discussed above) or other aspects of dynamical modeling (e.g., in connection with the program modeling system 720). As also illustrated, the dynamical system data processing 902 provides control and operation of programming determination logic 910, which utilizes the dynamic modeling results to perform aspects of program parameter identification 920, program selection 912, and program modification 914, using the dynamic models discussed herein.

The output of the programming determination logic may identify and effect the use of programming parameters 930 (e.g., treatment parameters 880) as part of treatment for a chronic pain condition using the neurostimulation device 750. As illustrated, the programming parameters 930 may include defined aspects such as amplitude, pulse type, pulse pattern, duration, and frequency, among other aspects described herein.

The inputs that can be provided to the dynamical system data processing 902 as part of a program selection process (e.g., with use of a dynamical model) may include: model parameters 900-1, relevant to the operation of the dynamic modeling; predicted pain 900-2, relevant to the particular predicted pain condition of the human subject; and observed patient pain 900-3, relevant to the current, historical, or previously observed pain condition of the patient. In an example, the observed patient pain 900-3 may be represented by a data value, measurement, or as a result of other data types, including values that indicate values or changes in pain level, pain area, spread of pain, or other pain characteristics. Further parameters include model time data 900-4, indicating time increments, measurements, or values relevant to the dynamical model; and stimulator input 900-5, which define the applicable universe or set of stimulator operations to be modeled. In an example, the parameters of the stimulator input 900-5 include a set of available stimulator programs 904, which define constraints of the available universe of programs operable with the neurostimulation device 750 and/or considered by the dynamical model.

As discussed above, the pain values (including observed patient pain 900-3) may be determined from various forms and types of patient sensor data 940, such as activity data, behavior data, or physiologic data. In an example, physiological data includes values to indicate at least one of: autonomic tone, heart rate, respiratory rate, or blood pressure, for the human subject. In another example, activity data includes values to indicate of at least one of: movement or gait for the human subject. Finally, in another example, behavior data includes values to indicate at least one of: a psychological state of the human subject or social activities performed by the human subject. Any combination of these data values may also be considered and used as part of the patient pain measurements 900-3 or the dynamical system data processing 902.

Figure 10:
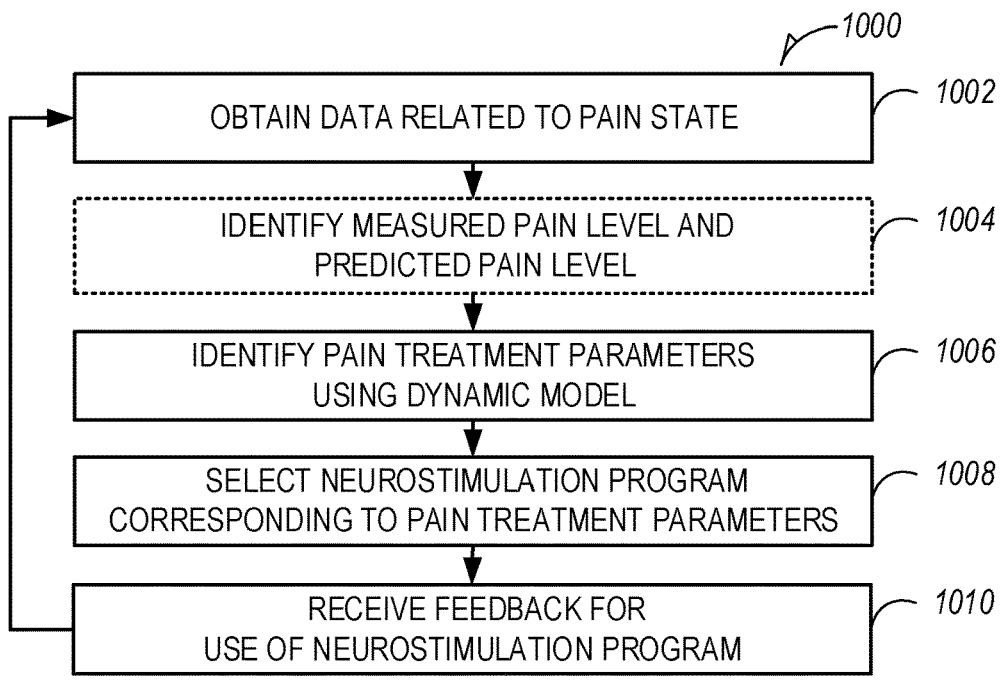
FIG. 10 illustrates, by way of example, an embodiment of a processing method implemented by a system or device for use to adjust programming of an implantable electrical neurostimulation device for treating chronic pain of a human subject.

FIG. 10 illustrates, by way of example, an embodiment of a processing method 1000 implemented by a system or device for use to adjust programming of an implantable electrical neurostimulation device for treating chronic pain of a human subject. For example, the processing method 1000 can be embodied by electronic operations performed by one or more computing systems or devices that are specially programmed to implement the pain determination, program modeling, and neurostimulation programming functions described herein.

For example, the method 1000 includes the obtaining (e.g., receiving, requesting, extracting, processing) of data related to a pain state of a human subject (e.g., patient) in connection with chronic pain treatment with a neurostimulation treatment (or series of treatments) (operation 1002). This data may represent or correspond to various forms of pain values, sensor measurements, device operational details, user input, indicated above for FIG. 9, although other formats and forms of data may also be may be used.

The method 1000 continues, in an optional example, with the identification of a measured pain level and/or a predicted pain level, from the data related to the pain state (operation 1004). Accordingly, in this optional example, operations that identify the pain treatment parameters may utilize the dynamic model to evaluate at least the measured pain level and the predicted pain level as part of determining pain treatment parameters or an appropriate program (further discussed below). In a further example (not depicted), the dynamic model is one of a plurality of dynamic models available for identification of the pain treatment parameters, such as in a case where the particular utilized dynamic model is selected from a dynamic model data source based on the data related to a state of pain of the human subject The method 1000 continues to identify one or more pain treatment parameters, using a dynamic model (operation 1006). The parameters of the dynamic model may include those described above in FIG. 9 (e.g., parameters 900-1 to 900-5). In an example, the dynamic model is a continuous time model or a discrete time model, such that the dynamic model evaluates the pain treatment parameters in the human subject over the time period based on: predicted pain of the human subject, observed pain of the human subject, dynamic model parameters, and operational data of the implantable electrical neurostimulation device. In a further example, the dynamic model is adapted to evaluate the pain treatment parameters in the human subject based on operational data obtained from use or programming of the implantable electrical neurostimulation device.

The method 1000 concludes to select a neurostimulation program corresponding to the pain treatment parameters (operation 1008). The selection of the neurostimulation program may be implemented within the dynamic model, programming determination logic, or other aspects of a programming or information system. In an example, the selected neurostimulation program is one of a plurality of predefined neurostimulation programs available for use in the implantable electrical neurostimulation device In an example, the selected neurostimulation program causes a change in operation of the implantable electrical neurostimulation device with the identified parameters, with such change corresponding to a change in the state of pain of the human subject. Also in an example, the selected neurostimulation program specifies a change in programming for the implantable electrical neurostimulation device, with the identified parameters, for one or more of: pulse patterns, pulse shapes, a spatial location of pulses, waveform shapes, or a spatial location of waveform shapes, for modulated energy provided with a plurality of leads of the implantable electrical neurostimulation device.

The method 1000 may continue with additional operations (not depicted) to cause the programming of the neurostimulation device with the selected program or the identified parameters. Such programming may be affected in the manner as described with FIG. 7 above, or with other variations involving the use of patient, clinician, or administrator involvement. Other variations to repeat the selection operations, incorporating patient feedback or clinician observations, or providing other aspects of identifying programs with the dynamic model, may be utilized.

Figure 11:
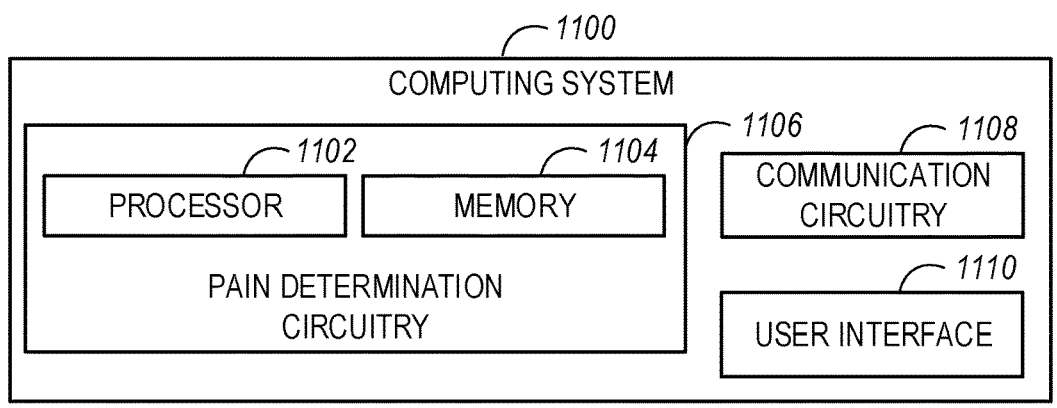
FIG. 11 illustrates, by way of example, a block diagram of an embodiment of a computing system implementing pain determination circuitry for use to adjust programming of an implantable electrical neurostimulation device for treating chronic pain of a human subject.

FIG. 11 illustrates, by way of example, a block diagram of an embodiment of a system 1100 (e.g., a computing system) for implementing adjustments of programming of an implantable electrical neurostimulation device for treating chronic pain of a human subject. The system 1100 may be a remote control device, patient programmer device, clinician programmer device, or other external device, usable for the determination of pain information in connection with dynamical modeling discussed herein. In some examples, the system 1100 may be a networked device connected via a network (or combination of networks) to a programming device or programming service using a communication interface 1108, with the programming device or programming service providing output content for the graphical user interface or responding to input of the graphical user interface. The network may include local, short-range, or long-range networks, such as Bluetooth, cellular, IEEE 802.11 (Wi-Fi), or other wired or wireless networks.

The system 1100 includes a processor 1102 and a memory 1104, which can be optionally included as part of pain determination circuitry 1106. The processor 1102 may be any single processor or group of processors that act cooperatively. The memory 1104 may be any type of memory, including volatile or non-volatile memory. The memory 1104 may include instructions, which when executed by the processor 1102, cause the processor 1102 to implement the features of the user interface, or to enable other features of the pain determination circuitry 1106. Thus, electronic operations in the system 1100 may be performed by the processor 1102 or the circuitry 1106.

For example, the processor 1102 or circuitry 1106 may implement any of the features of the method 1000 (including operations 1002, 1004, 1006) to obtain data related to a pain state, identify a pain level, or identify pain treatment parameters, in connection with a neurostimulation program or treatment. The processor 1102 or circuitry 1106 may further transmit the pain treatment parameters or the operational program directly to a neurostimulation device (or to a programming device or system that in turn communicates and implements the modification to the neurostimulation device). It will be understood that the processor 1102 or circuitry 1106 may also implement other aspects of the logic and processing described above with reference to FIGS. 7-9.

Figure 12:
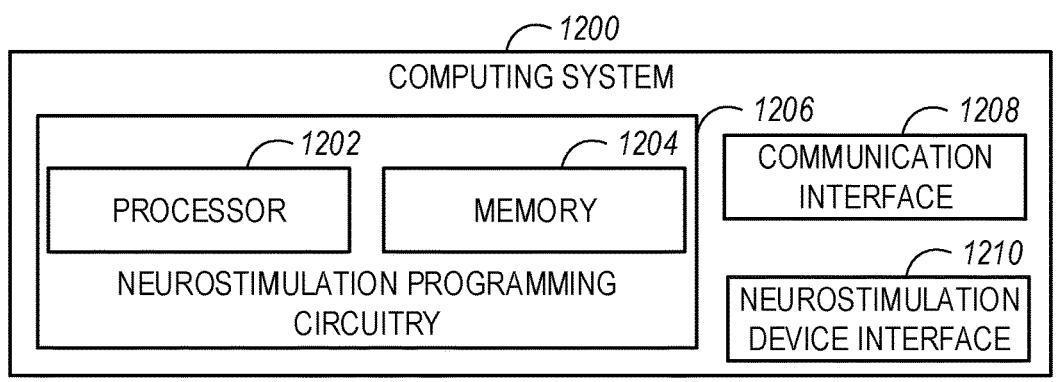
FIG. 12 illustrates, by way of example, a block diagram of an embodiment of a computing system implementing neurostimulation programming circuitry for use to adjust programming of an implantable electrical neurostimulation device for treating chronic pain of a human subject.

FIG. 12 illustrates, by way of example, a block diagram of an embodiment of a system 1200 (e.g., a computing system) for implementing adjustments of programming of an implantable electrical neurostimulation device for treating chronic pain of a human subject. The system 1200 may be operated by a clinician, a patient, a caregiver, a medical facility, a research institution, a medical device manufacturer or distributor, and embodied in a number of different computing platforms. The system 1200 may be a remote control device, patient programmer device, program modeling system, or other external device used by a patient, including a regulated device used to directly implement programming commands and modification with a neurostimulation device. In some examples, the system 1200 may be a networked device connected via a network (or combination of networks) to a computing system operating a user interface computing system using a communication interface 1208. The network may include local, short-range, or long-range networks, such as Bluetooth, cellular, IEEE 802.11 (Wi-Fi), or other wired or wireless networks.

The system 1200 includes a processor 1202 and a memory 1204, which can be optionally included as part of neurostimulation programming circuitry 1206. The processor 1202 may be any single processor or group of processors that act cooperatively. The memory 1204 may be any type of memory, including volatile or non-volatile memory. The memory 1204 may include instructions, which when executed by the processor 1202, cause the processor 1202 to implement the features of the programming device, or to enable other features of the programming modification logic and programming circuitry 1206. Thus, the following references to electronic operations in the system 1200 may be performed by the processor 1202 or the circuitry 1206.

For example, the processor 1202 or circuitry 1206 may implement any of the features of the method 1000 (including operations 1008, 1010) to select a neurostimulation program, transmit the operational program to the neurostimulation device, implement (e.g., save, persist, activate, control) the modification of the operational program in the neurostimulation device, and receive feedback for use of the neurostimulation program, all with use of a neurostimulation device interface 1210. The processor 1202 or circuitry 1206 may further provide data and commands to assist the processing and implementation of the programming using communication interface 1208. It will be understood that the processor 1202 or circuitry 1206 may also implement other aspects of the programming devices and device interfaces described above with reference to FIGS. 7-9.

Figure 13:
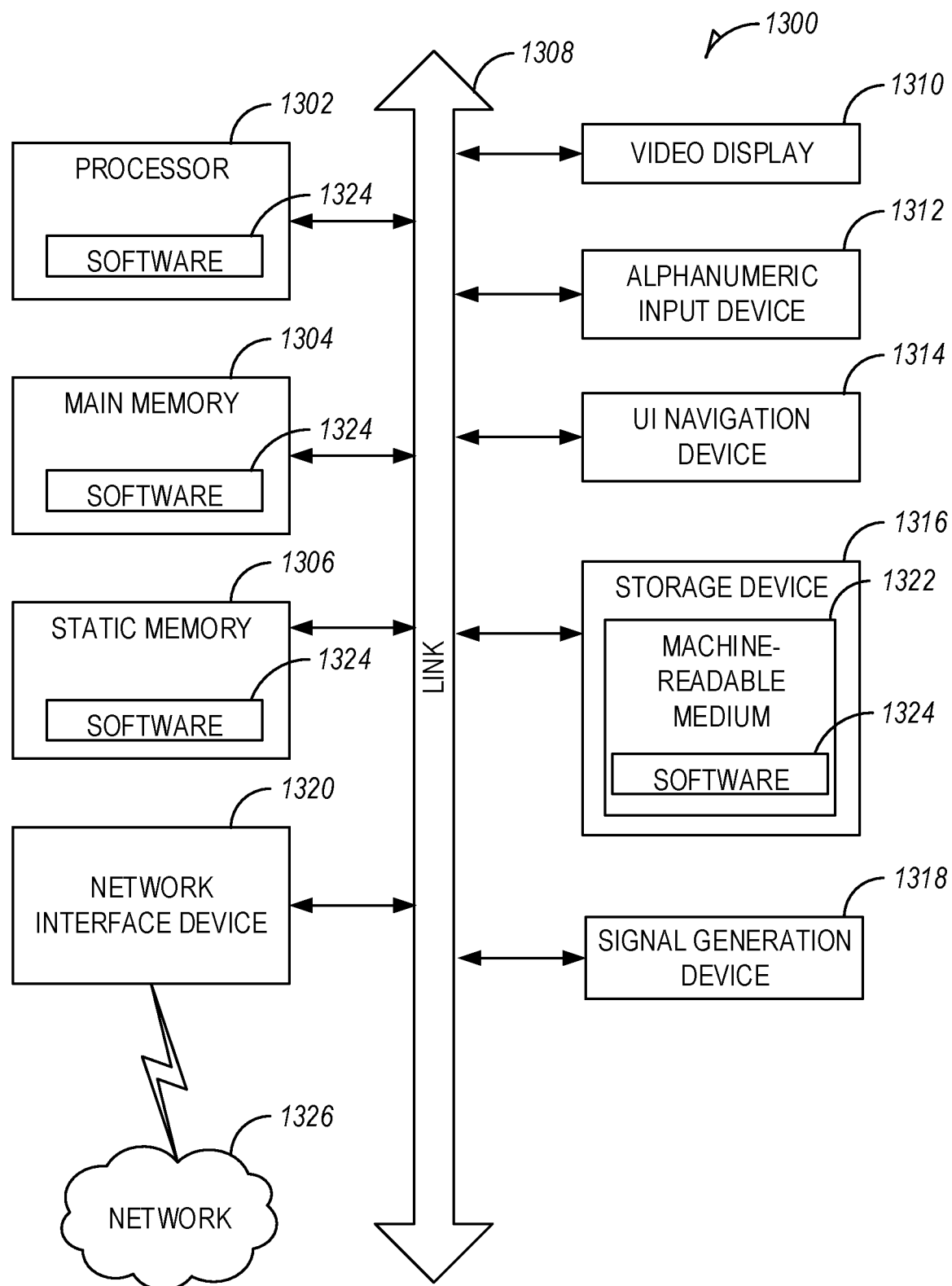
FIG. 13 is a block diagram illustrating a machine in the example form of a computer system, within which a set or sequence of instructions may be executed to cause the machine to perform any one of the methodologies discussed herein, according to an example embodiment.

FIG. 13 is a block diagram illustrating a machine in the example form of a computer system 1300, within which a set or sequence of instructions may be executed to cause the machine to perform any one of the methodologies discussed herein, according to an example embodiment. In alternative embodiments, the machine operates as a standalone device or may be connected (e.g., networked) to other machines. In a networked deployment, the machine may operate in the capacity of either a server or a client machine in server-client network environments, or it may act as a peer machine in peer-to-peer (or distributed) network environments. The machine may be a personal computer (PC), a tablet PC, a hybrid tablet, a personal digital assistant (PDA), a mobile telephone, an implantable pulse generator (IPG), an external remote control (RC), a User's Programmer (CP), or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein. Similarly, the term "processor-based system" shall be taken to include any set of one or more machines that are controlled by or operated by a processor (e.g., a computer) to individually or jointly execute instructions to perform any one or more of the methodologies discussed herein.

Example computer system 1300 includes at least one processor 1302 (e.g., a central processing unit (CPU), a graphics processing unit (GPU) or both, processor cores, compute nodes, etc.), a main memory 1304 and a static memory 1306, which communicate with each other via a link 1308 (e.g., bus). The computer system 1300 may further include a video display unit 1310, an alphanumeric input device 1312 (e.g., a keyboard), and a user interface (UI) navigation device 1314 (e.g., a mouse). In one embodiment, the video display unit 1310, input device 1312 and UI navigation device 1314 are incorporated into a touch screen display. The computer system 1300 may additionally include a storage device 1316 (e.g., a drive unit), a signal generation device 1318 (e.g., a speaker), a network interface device 1320, and one or more sensors (not shown), such as a global positioning system (GPS) sensor, compass, accelerometer, or other sensor. It will be understood that other forms of machines or apparatuses (such as PIG, RC, CP devices, and the like) that are capable of implementing the methodologies discussed in this disclosure may not incorporate or utilize every component depicted in FIG. 13 (such as a GPU, video display unit, keyboard, etc.).

The storage device 1316 includes a machine-readable medium 1322 on which is stored one or more sets of data structures and instructions 1324 (e.g., software) embodying or utilized by any one or more of the methodologies or functions described herein. The instructions 1324 may also reside, completely or at least partially, within the main memory 1304, static memory 1306, and/or within the processor 1302 during execution thereof by the computer system 1300, with the main memory 1304, static memory 1306, and the processor 1302 also constituting machine-readable media.

While the machine-readable medium 1322 is illustrated in an example embodiment to be a single medium, the term "machine-readable medium" may include a single medium or multiple media (e.g., a centralized or distributed database, and/or associated caches and servers) that store the one or more instructions 1324. The term "machine-readable medium" shall also be taken to include any tangible (e.g., non-transitory) medium that is capable of storing, encoding or carrying instructions for execution by the machine and that cause the machine to perform any one or more of the methodologies of the present disclosure or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including but not limited to, by way of example, semiconductor memory devices (e.g., electrically programmable read-only memory (EPROM), electrically erasable programmable read-only memory (EEPROM)) and flash memory devices; magnetic disks such as internal hard disks and removable disks; magneto-optical disks; and CD-ROM and DVD-ROM disks.

The instructions 1324 may further be transmitted or received over a communications network 1326 using a transmission medium via the network interface device 1320 utilizing any one of a number of well-known transfer protocols (e.g., HTTP). Examples of communication networks include a local area network (LAN), a wide area network (WAN), the Internet, mobile telephone networks, plain old telephone (POTS) networks, and wireless data networks (e.g., Wi-Fi, 3G, and 4G LTE/LTE-A or 5G networks). The term "transmission medium" shall be taken to include any intangible medium that is capable of storing, encoding, or carrying instructions for execution by the machine, and includes digital or analog communications signals or other intangible medium to facilitate communication of such software.

The above detailed description is intended to be illustrative, and not restrictive. The scope of the disclosure should, therefore, be determined with references to the appended claims, along with the full scope of equivalents to which such claims are entitled.

What is claimed is:

1. A device to adjust programming of an implantable electrical neurostimulation device for treating chronic pain of a human subject, the device comprising:
   at least one processor and at least one memory;
   pain determination circuitry, operable with the processor and the memory, configured to:
      obtain data related to a state of pain from a chronic pain condition of the human subject;
      identify a new set of pain treatment parameters, using a dynamic model, that are not in use in a program of the implantable electrical neurostimulation device, the dynamic model adapted to evaluate the new set of pain treatment parameters in the human subject over a modeled time period,
      wherein the dynamic model evaluates modeled parameter combinations that are customized to the human subject to identify the new set of pain treatment parameters that provide an improvement in an observed pain condition relative to an existing set of pain treatment parameters, when applied in treatment of the chronic pain condition for the human subject, and
      wherein the dynamic model identifies first or second order dynamics within a discrete series or continuous integral of time windows in the modeled time period, for each of the modeled parameter combinations, to analyze a pain state from use of the modeled parameter combinations during the modeled time period, based on: values of a predicted pain condition of the human subject, and values of the observed pain condition determined from the obtained data related to the state of pain of the human subject; and
   neurostimulation programming circuitry, in operation with the at least one processor and the at least one memory, configured to:
      select a neurostimulation program for the implantable electrical neurostimulation device, the neurostimulation program corresponding to at least a portion of the new set of pain treatment parameters identified by the dynamic model.

2. The device of claim 1, the pain determination circuitry further configured to:
identify a measured pain level and a predicted pain level of the human subject using the data related to the state of pain;
wherein operations that identify the new set of pain treatment parameters using the dynamic model evaluate at least the measured pain level and the predicted pain level; and
wherein the data related to the state of pain of the human subject comprises data obtained from the human subject that includes at least one of: physiological data, activity data, or behavior data.

3. The device of claim 1, the pain determination circuitry further configured to:
identify the state of pain of the human subject from evaluation of one or more of:
(a) physiological data for the human subject that includes values to indicate at least one of: autonomic tone, heart rate, respiratory rate, or blood pressure;
(b) activity data for the human subject that includes values to indicate of at least one of: movement or gait; or
(c) behavior data for the human subject that includes values to indicate at least one of: a psychological state of the human subject or social activities performed by the human subject.

4. The device of claim 1, the pain determination circuitry further configured to:
evaluate the new set of pain treatment parameters in the human subject, with the dynamic model, based on operational data obtained from use or programming of the implantable electrical neurostimulation device in the human subject.

5. The device of claim 1,
wherein the dynamic model is a continuous time model using dynamic equations to evaluate the modeled parameter combinations with a continuous time period or a discrete time model using dynamic equations to evaluate the modeled parameter combinations with a discrete time period, wherein the dynamic model evaluates the modeled parameter combinations in the human subject over the modeled time period based on: predicted pain of the human subject, observed pain of the human subject, dynamic model parameters, and operational data of the implantable electrical neurostimulation device.

6. The device of claim 1, further comprising user interface circuitry, in operation with the at least one processor and the at least one memory, configured to:
receive, from the human subject, feedback data on the selected neurostimulation program, the feedback data received in response to deployment of the selected neurostimulation program to the human subject using the implantable electrical neurostimulation device;
wherein subsequent operations using the dynamic model evaluate the feedback data as dynamic model parameters.

7. The device of claim 6,
wherein a user interface implemented with the user interface circuitry is used to receive at least one of: at least a portion of the data related to a state of pain of the human subject, or a command to cause selection or deployment of the neurostimulation program.

8. The device of claim 1, further comprising communications circuitry, in operation with the at least one processor and the at least one memory;
wherein the new set of pain treatment parameters are stored by a data service, and
wherein subsequent operations using the dynamic model obtain the new set of pain treatment parameters from the data service and evaluate the new set of pain treatment parameters received from the data service using the communications circuitry.

9. The device of claim 1,
wherein the selected neurostimulation program is one of a plurality of predefined neurostimulation programs available for use in the implantable electrical neurostimulation device; and
wherein the dynamic model is one of a plurality of dynamic models available for identification of the new set of pain treatment parameters, and wherein the dynamic model is selected from a dynamic model data source based on the data related to a state of pain of the human subject.

10. The device of claim 1,
wherein the implantable electrical neurostimulation device is further configured to treat pain by delivering at least one of: an electrical spinal cord stimulation, an electrical brain stimulation, or an electrical peripheral nerve stimulation, in the human subject; and
wherein the new set of pain treatment parameters of the selected neurostimulation program specifies a change in programming for modulated energy provided with a plurality of leads of the implantable electrical neurostimulation device, the change in programming specified for one or more of: pulse patterns, pulse shapes, a spatial location of pulses, waveform shapes, or a spatial location of waveform shapes.

11. A method, for adjusting programming of an implantable electrical neurostimulation device for treating chronic pain of a human subject, the method comprising a plurality of operations executed with at least one processor of an electronic device, the plurality of operations comprising:
obtaining data related to a state of pain from a chronic pain condition of the human subject;
identifying a new set of pain treatment parameters, using a dynamic model, that are not in use in a program of the implantable electrical neurostimulation device, the dynamic model adapted to evaluate the new set of pain treatment parameters in the human subject over a modeled time period,
wherein the dynamic model evaluates modeled parameter combinations that are customized to the human subject to identify the new set of pain treatment parameters that provide an improvement in an observed pain condition relative to an existing set of pain treatment parameters, when applied in treatment of the chronic pain condition for the human subject, and
wherein the dynamic model identifies first or second order dynamics within a discrete series or continuous integral of time windows in a modeled time period, for each of the modeled parameter combinations, to analyze a pain state from use of the modeled parameter combinations during the modeled time period, based on: values of a predicted pain condition of the human subject, and values of the observed pain condition determined from the obtained data related to the state of pain of the human subject; and
selecting a neurostimulation program for the implantable electrical neurostimulation device, the neurostimulation program corresponding to at least a portion of the new set of pain treatment parameters identified by the dynamic model.

12. The method of claim 11, the operations further comprising:
identifying a measured pain level and a predicted pain level of the human subject using the data related to the state of pain;
wherein the operations that identify the new set of pain treatment parameters using the dynamic model evaluate at least the measured pain level and the predicted pain level; and
wherein the data related to the state of pain of the human subject comprises data obtained from the human subject that includes at least one of: physiological data, activity data, or behavior data.

13. The method of claim 11, the operations further comprising:
determining the state of pain of the human subject from evaluation of one or more of:
(a) physiological data for the human subject that includes values to indicate at least one of: autonomic tone, heart rate, respiratory rate, or blood pressure;
(b) activity data for the human subject that includes values to indicate of at least one of: movement or gait; or
(c) behavior data for the human subject that includes values to indicate at least one of: a psychological state of the human subject or social activities performed by the human subject.

14. The method of claim 11, the operations further comprising:
evaluating the new set of pain treatment parameters in the human subject, with the dynamic model, based on operational data obtained from use or programming of the implantable electrical neurostimulation device in the human subject.

15. The method of claim 11,
wherein the dynamic model is a continuous time model using dynamic equations to evaluate the modeled parameter combinations with a continuous time period or a discrete time model using dynamic equations to evaluate the modeled parameter combinations with a discrete time period, wherein the dynamic model evaluates the modeled parameter combinations in the human subject over the modeled time period based on: predicted pain of the human subject, observed pain of the human subject, dynamic model parameters, and operational data of the implantable electrical neurostimulation device.

16. The method of claim 11, the operations further comprising:
receiving, from the human subject, feedback data on the selected neurostimulation program, the feedback data received in response to deployment of the selected neurostimulation program to the human subject using the implantable electrical neurostimulation device;
wherein subsequent operations using the dynamic model evaluate the feedback data as dynamic model parameters.

17. The method of claim 11,
wherein the new set of pain treatment parameters are stored by a data service, and
wherein subsequent operations using the dynamic model obtain the new set of pain treatment parameters from the data service and evaluate the new set of pain treatment parameters obtained from the data service.

18. The method of claim 11,
wherein a user interface is used to receive at least one of: at least a portion of the data related to a state of pain of the human subject, or a command to cause selection or deployment of the neurostimulation program.

19. The method of claim 11,
wherein the selected neurostimulation program is one of a plurality of predefined neurostimulation programs available for use in the implantable electrical neurostimulation device; and
wherein the dynamic model is one of a plurality of dynamic models available for identification of the new set of pain treatment parameters, and wherein the dynamic model is selected from a dynamic model data source based on the data related to a state of pain of the human subject.

20. The method of claim 11,
wherein the new set of pain treatment parameters of the selected neurostimulation program cause a change in operation of the implantable electrical neurostimulation device, that corresponds to a change in the state of pain of the human subject; and
wherein the new set of pain treatment parameters of the selected neurostimulation program specifies a change in programming for modulated energy provided with a plurality of leads of the implantable electrical neurostimulation device, the change in programming specified for one or more of: pulse patterns, pulse shapes, a spatial location of pulses, waveform shapes, or a spatial location of waveform shapes.

* * * * *